United States Patent
Sornborger et al.

(10) Patent No.: US 8,265,360 B2
(45) Date of Patent: Sep. 11, 2012

(54) METHODS AND SYSTEMS FOR ANALYZING RATIOMETRIC DATA

(75) Inventors: Andrew T. Sornborger, Athens, GA (US); James D. Lauderdale, Statham, GA (US); Charles H. Keith, Bluffton, SC (US); Josef M. Broder, Ithaca, NY (US); Jeremy L. Praissman, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1019 days.

(21) Appl. No.: 12/200,046

(22) Filed: Aug. 28, 2008

(65) Prior Publication Data
US 2009/0060266 A1 Mar. 5, 2009

Related U.S. Application Data

(60) Provisional application No. 60/967,038, filed on Aug. 31, 2007.

(51) Int. Cl.
G06K 9/00 (2006.01)
G06K 9/64 (2006.01)
G01B 11/00 (2006.01)

(52) U.S. Cl. ........ 382/128; 382/130; 382/131; 382/132; 382/133; 382/191; 382/278

(58) Field of Classification Search ................... 382/128, 382/130, 131, 132, 191, 278, 133
See application file for complete search history.

(56) References Cited

U.S. PATENT DOCUMENTS 5,485,530 A * 1/1996 Lakowicz et al. ............. 382/191
5,995,645 A * 11/1999 Soenksen et al. ............. 382/133
6,055,325 A * 4/2000 Garini et al. .................. 382/129
6,546,146 B1 * 4/2003 Hollinger et al. ............. 382/253
6,593,101 B2 * 7/2003 Richards-Kortum et al. .. 435/29
2002/0146160 A1 * 10/2002 Parker et al. .................. 382/131

OTHER PUBLICATIONS

Madsen, et al. (2004). Singular value decomposition and principal component analysis. Informally published manuscript, Department of Informatics and Mathematical Modelling, Technical University of Denmark, Lynbgy, Denmark. Retrieved from http://www2.imm.dtu.dk/pubdb/views/edoc_download.php/4000/pdf/imm4000.pdf.*
Subramanian, et al. "Methodology for Hyperspectral Image Classification Using Novel Neural Network." Algorithms for Multispectral and Hyperspectral Imagery III, SPIE. 3071. (1997): 1-10. Print.*
Madsen et al. (2004). Singular value decomposition and principal component analysis. Informally published manuscript, Department of Informatics and Mathematical Modeling, Technical University of Denmark, Lynbgy, Denmark. Retrieved from http://www2.imm.dtu.dk/pubdb/views/edoc_download.php/4000/pdf/imm4000.pdf.*
Fodor, Imola K. United States. Survey of Dimension Reduction Techniques. Livermore, CA: , 2002. Web. <https://computation.llnl.gov/casc/sapphire/pubs/148494.pdf>.*

(Continued)

*Primary Examiner* — Michael A Newman
(74) *Attorney, Agent, or Firm* — Mueting Raasch & Gebhardt, P.A.

(57) ABSTRACT

Systems and methods for analyzing ratiometric data, e.g., ratiometric image data such as fluorescent image data, may generate a correlation matrix for the ratiometric data, generate a plurality of eigenvalues and a plurality of eigenvectors based on the correlation matrix, select a set of eigenvectors from the plurality of eigenvectors, and reconstruct a set of enhanced ratiometric data for use in analysis.

43 Claims, 17 Drawing Sheets

OTHER PUBLICATIONS

Anderson, *An Introduction to Multivariate Statistical Analysis*, 2$^{nd}$ Edition John Wiley & Sons: New York, NY; 1984. Cover page, publishers page, and table of contents only. 10 pages.

Broder, "Multivariate methods for the analysis of multichannel NADH/Flavoprotein and ratiometric calcium imaging signals," Poster Abstract No. 457.9. *2005 Abstract Viewer/Itinerary Planner*; Presented at the 2005 Neuroscience Meeting (Society for Neuroscience) Washington DC: Nov. 12-16, 2005.

Broder et al., "Estimating weak ratiometric signals in imaging data. I. Dual-channel data," Sep. 2007 *J. Opt. Soc. Am. A* 24(9):2921-2931.

Carroll, "Generalization of canonical correlation analysis to three or more sets of variables," *Proc. 76th Ann. Conv. APA* pp. 227-228 (1968).

Hanks, "Hank's balanced salt solution and pH control," 1976 *Tissue Culture Association Manual* 1(1):3-4.

Hotelling, "Relations between two sets of variates," 1936 *Biometrika* 28:321-377.

Percival and Walden, *Spectral Analysis for Physical Applications: Multitaper and Conventional Univariate Techniques* Cambridge University Press: Cambridge, UK; 1993. Cover page, publishers page, and table of contents only. 7 pages.

Sornborger, "Between group analysis of calcium imaging data using canonical variate analysis," [online]. Poster Abstract No. 492. *2006 Abstract Viewer/Itinerary Planner*; Presented at the 2006 Neuroscience Meeting (Society for Neuroscience) Atlanta, GA: Oct. 14-18, 2006. Available online on Sep. 1, 2006 [retrieved on Apr. 4, 2007]. Retrieved from the Internet: <http://www.abstractsonline.com/viewer/SearchResults.asp>; 2 pgs.

Sornborger et al., "Estimating weak ratiometric signals in imaging data. II: Meta-analysis with multiple, dual-channel datasets," Sep. 2008 *J. Opt. Soc. Am. A* 25(9):2185-2194.

Sornborger, Andrew, "Intrinsic Fluorometric Imaging at the Cellular and System Levels," Grant Abstract, Grant No. 1R21EB005432-01A1 [online]. National Institutes of Health; National Institute of Biomedical Imaging and Bioengineering. Project dates Jun. 1, 2006 to May 31, 2008 [retrieved on Jul. 13, 2007]. Retrieved from the Internet: <http://crisp.cit.nih.gov/crisp/CRISP_LIB.getdoc?textkey=7091861&p_grant_num=1R21EB005432-01A1&p_query=&ticket=91677338&p_audit_session_id=419916379&p_keywords=>; 2 pgs.

Sornborger, Andrew, "Intrinsic Fluorometric Imaging at the Cellular and System Levels," Grant Abstract, Grant No. 5R21EB005432-02 [online]. National Institutes of Health; National Institute of Biomedical Imaging and Bioengineering. Project dates Jun. 1, 2006 to May 31, 2008 [retrieved on Jul. 13, 2007]. Retrieved from the Internet: <http://crisp.cit.nih.gov/crisp/CRISP_LIB.getdoc?textkey=7230189&p_grant_num=5R21EB005432-02&p_query=&ticket=91677338&p_audit_session_id=419916379&p_keywords=>; 1 pg.

Truong et al., "FRET-based in vivo $Ca^{2+}$ imaging by a new calmodulin-GFP fusion molecule," Dec. 2001 *Nat. Struct. Bio.* 8(12):1069-1073.

\* cited by examiner

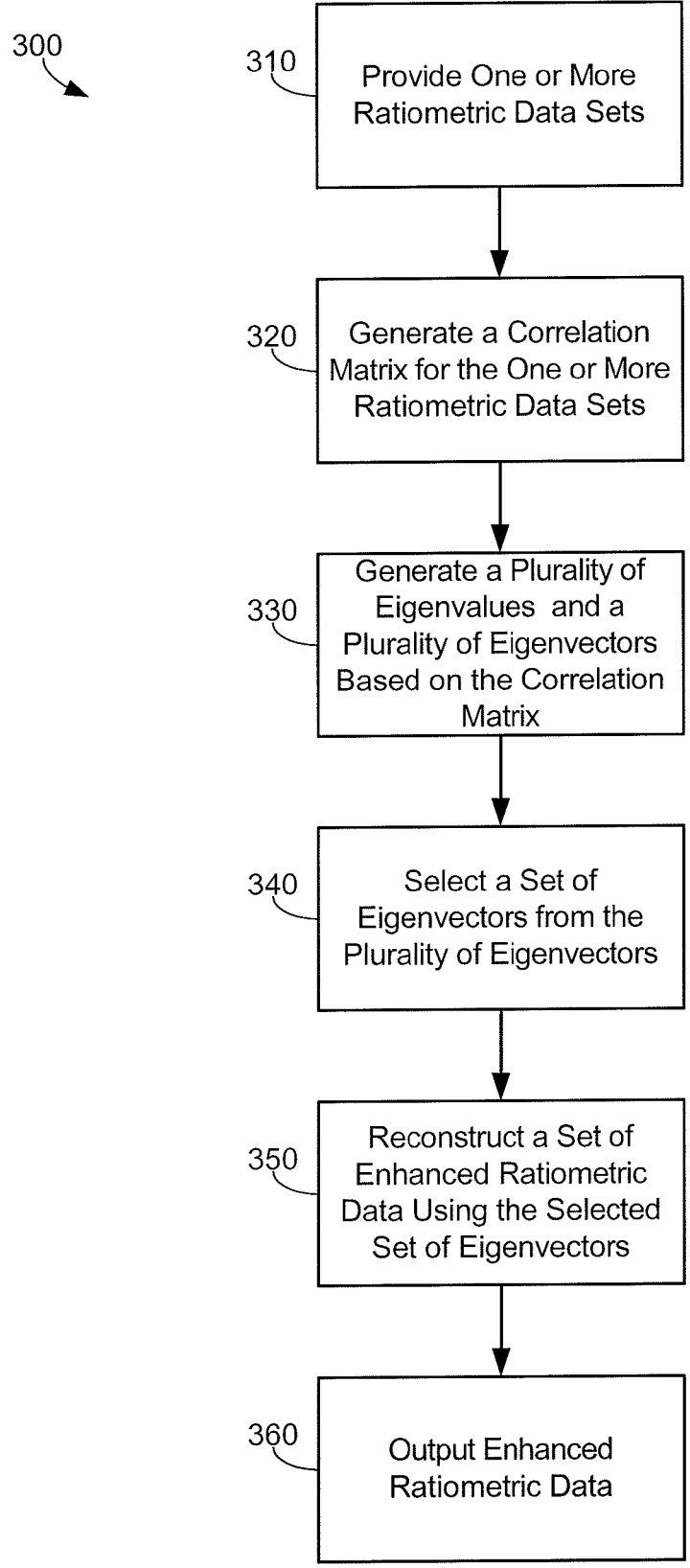

METHODS AND SYSTEMS FOR ANALYZING RATIOMETRIC DATA

CROSS-REFERENCE TO RELATED APPLICATIONS

This application claims the benefit of U.S. Provisional Application Ser. No. 60/967,038 filed 31 Aug. 2007, entitled "Method for Detecting and Estimating Ratiometric Signals," which is incorporated herein by reference in its entirety.

STATEMENT OF GOVERNMENT RIGHTS

This invention was made with government support under a grant from the National Institutes of Health (Grant No R21 EB005432). The U.S. Government has certain rights in this invention.

BACKGROUND

The present invention generally relates to the analysis of ratiometric data, e.g., ratiometric image data such as fluorescent image data.

Ratiometric imaging, for example, may include the acquisition of fluorescent images at two different wavelengths. At one wavelength, for example, a change or changes in a variable of interest (e.g., composition or object being imaged) may cause a fractional change in the fluorescence intensity, while at the other wavelength, the fluorescence intensity may either change opposite to the change in the first wavelength, or the fluorescence may remain unchanged. In other words, the signals are either anti-correlated or divergent. Problems can arise when the ratiometric image series are noisy and/or the signals are weak. For example, noise may cause the denominator in the ratio (e.g., of the ratiometric data) to become excessively small, making the ratio to be excessively (and spuriously) large.

A method of analyzing a single ratiometric dataset using singular value decomposition to find covarying information has previously been investigated (see, e.g., J. Broder, A. Majumder, C. H. Keith, J. D. Lauderdale and A. Sornborger, "Multivariate methods for the analysis of multichannel NADH/Flavoprotein and ratiometric calcium imaging signals," Poster: Program No. 457.9, 2005 Abstract Viewer/Itinerary Planner, Washington, D.C., Society for Neuroscience).

Methods of finding correlated information across multiple datasets have previously been investigated. For example, Hotelling investigated finding correlated information across two datasets (see, e.g., 2. H. Hotelling, "Relations between two sets of variates," Biometrika 28:321-377 (1936)). Also, for example, Carroll investigated finding correlated information across multiple datasets (see, e.g., J. D. Carroll, "Generalization of canonical correlation analysis to three or more sets of variables," Proc. 76th Ann. Conv. APA pp. 227-228 (1968)).

SUMMARY

Generally, the present invention includes one or more processes or programs (or systems including such programs). For example, the present invention may be considered to include multiple processes or programs that may be implemented alone or in combination. Further, the output of one program or process may be used as an input by another program described herein or any other program that may operate on the input, the input to the process described herein may be received from an output of another process, or the multiple processes may be used in any other effective combination.

In one computer-implemented method of the present invention for use in analysis of image data, the computer-implemented method includes providing a ratiometric dataset representative of image data obtained over time for use in analysis of one or more objects of interest. Providing the ratiometric dataset includes providing a first wavelength dataset representative of image data taken over time at a first wavelength, providing a second wavelength dataset representative of image data taken over time at a second wavelength, and comparing the first wavelength dataset with the second wavelength dataset to provide the ratiometric dataset. Further, the method includes generating a correlation matrix (e.g., temporal or spectral) for the ratiometric dataset, generating a plurality of eigenvalues and a plurality of eigenvectors based on the correlation matrix, and selecting a set of eigenvectors from the plurality of eigenvectors. Still further, the method includes reconstructing a set of enhanced ratiometric images for use in analysis of the one or more objects of interest, wherein the set of enhanced ratiometric images is reconstructed using the set of eigenvectors, the first wavelength dataset, and the second wavelength dataset.

In another computer-implemented method of the present invention for use in analysis of image data, the computer-implemented method includes providing two or more ratiometric datasets representative of image data obtained over time for use in analysis of one or more objects of interest. Providing each of the two or more ratiometric datasets includes providing a first wavelength dataset representative of image data taken over time at a first wavelength, providing a second wavelength dataset representative of image data taken over time at a second wavelength, and comparing the first wavelength dataset with the second wavelength dataset to provide each of the two or more ratiometric datasets. Further, the method includes generating a correlation matrix (e.g., temporal or spectral) for each of the two or more ratiometric datasets, generating a summed correlation matrix by summing the correlation matrices generated for each of the two or more ratiometric datasets, generating a plurality of eigenvalues and a plurality of eigenvectors based on the summed correlation matrix, and selecting a set of eigenvectors from the plurality of eigenvectors. Still further, the method includes reconstructing at least one set of enhanced ratiometric images for use in analysis of the one or more objects of interest, each set of enhanced ratiometric images corresponding to a ratiometric dataset of the two or more ratiometric datasets, wherein the at least one set of enhanced ratiometric images is reconstructed using the set of eigenvectors and the first and second wavelength dataset used to provide the corresponding ratiometric dataset.

In still another computer-implemented method of the present invention for use in analysis of measurement data, the computer-implemented method includes providing one or more ratiometric datasets representative of measurement data obtained over time for use in analysis of one or more objects of interest. Providing each of the one or more ratiometric datasets includes providing a first dataset representative of measurement data taken over time, providing a second dataset representative of measurement data taken over time, and comparing the first dataset with the second dataset to provide each of the one or more ratiometric datasets. Further, the method includes generating a correlation matrix (e.g., temporal or spectral) for the one or more ratiometric datasets, generating a plurality of eigenvalues and a plurality of eigenvectors based on the correlation matrix, and selecting a set of eigenvectors from the plurality of eigenvectors. Still further, the method includes reconstructing at least one set of enhanced ratiometric measurement data for use in analysis of the one or more objects of interest, each set of enhanced ratiometric measurement data corresponding to a ratiometric dataset of the one or more ratiometric datasets, wherein the at least one set of enhanced ratiometric measurement data is reconstructed using the set of eigenvectors and the first and second dataset used to provide the corresponding ratiometric dataset.

A computer program for use in conjunction with a processing apparatus to analyze ratiometric data is also provided. The computer program is operable when used with the processing apparatus to recognize one or more ratiometric datasets representative of measurement data obtained over time for use in analysis of one or more objects of interest. Each of the one or more ratiometric datasets includes a first dataset representative of measurement data taken over time compared with a second dataset representative of measurement data taken over time. Further, the computer program is operable to generate a correlation matrix (e.g., temporal or spectral) for the one or more ratiometric datasets, generate a plurality of eigenvalues and a plurality of eigenvectors based on the correlation matrix, and select a set of eigenvectors from the plurality of eigenvectors. Still further, the computer program is operable to reconstruct at least one set of enhanced ratiometric measurement data for use in analysis of the one or more objects of interest, each set of enhanced ratiometric measurement data corresponding to a ratiometric dataset of the one or more ratiometric datasets, wherein the at least one set of enhanced ratiometric measurement data is reconstructed using the set of eigenvectors and the first and second dataset used to provide the corresponding ratiometric dataset.

In one or more embodiments according to the present invention, the computer-implemented methods, systems, or programs further include outputting enhanced ratiometric data (e.g., enhanced images) to at least one of a user, a display, and a file (e.g., a file in user-readable format).

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

FIG. 3 shows a more detailed block diagram of one illustrative embodiment of a method for analyzing ratiometric data as generally illustrated in the method of FIG. 2.

DETAILED DESCRIPTION OF EXEMPLARY EMBODIMENTS

Figure 1:
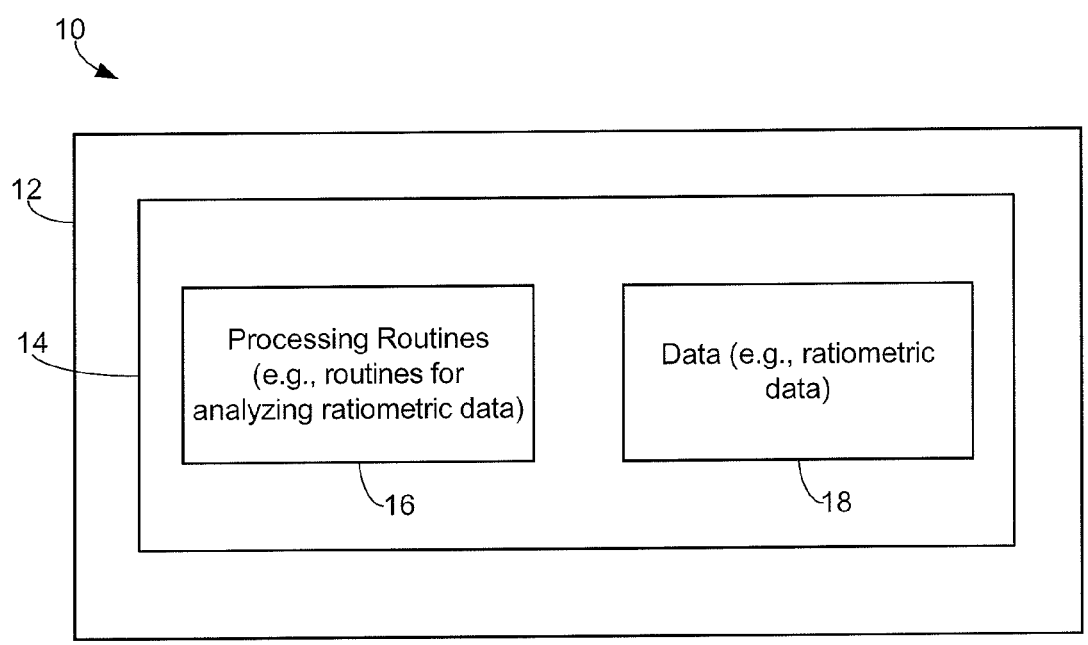
FIG. 1 shows a general block diagram of a general illustrative data processing system for use in analysis of data according to the present invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and changes may be made without departing from the scope of the present invention.

FIG. 1 shows a data analysis system 10 including a processing apparatus (block 12) and data storage (block 14).

Figure 2:
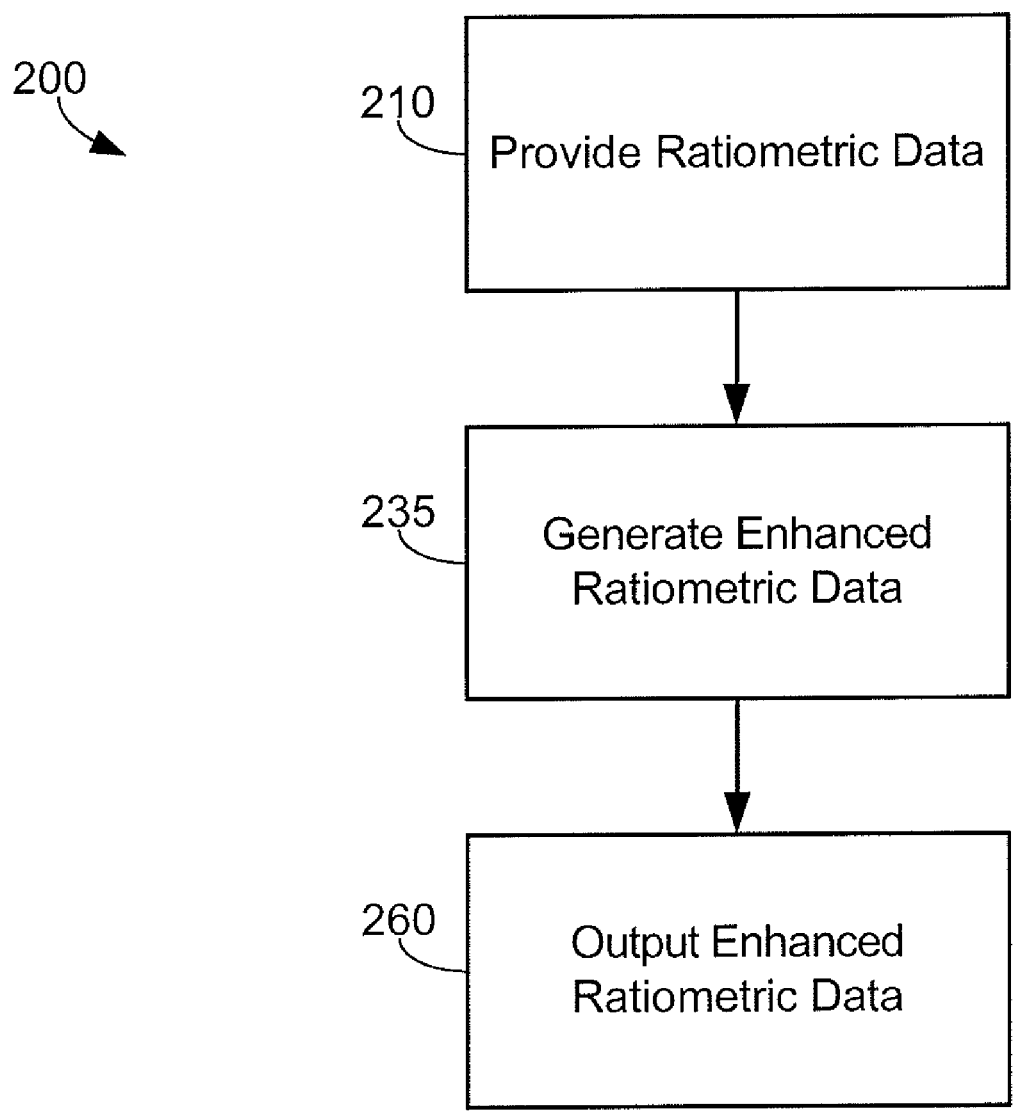
FIG. 2 shows a general block diagram of a general illustrative data processing method for analyzing ratiometric data according to the present invention.

Data storage (block 14) allows for access to processing programs or routines (block 16) and one or more other types of data (block 18) that may be employed to carry out the illustrative ratiometric data analysis method (block 200) as shown generally in the block diagram of FIG. 2.

For example, processing programs or routines (block 16) may include programs or routines for performing matrix mathematics, compression algorithms, standardization algorithms, comparison algorithms, vector mathematics, or any other processing required to implement one or more embodiments of the present invention as described herein. Data (block 18) may include, for example, wavelength data representative of image data taken over time, data representative of measurement data taken over time, ratiometric data, results from one or more processing programs or routines employed according to the present invention, or any other data that may be necessary for carrying out the one or more processes described herein.

As used herein, ratiometric data refers to any data generated by comparing a first set of measurement data taken over a length of time (e.g., a first dataset representative of image data obtained over time) to a second set of measurement data taken over the same length of time (e.g., a second dataset representative of image data obtained over time). In one or more embodiments, a ratiometric dataset includes measurements to the same stimulus protocol. In other words, at least in one embodiment, the datasets represent differential measurements over time, e.g., two variables that are expected to diverge in response to the same stimulus over time.

In one or more embodiments of the present invention, the data analysis system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The program used to implement the present invention may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein.

Likewise, the data analysis system 10 may be configured at a remote site (e.g., an application server) that allows access by one or more users via a remote computer apparatus (e.g., via a web browser), and allows a user to employ the functionality according to the present invention (e.g., user accesses a graphical user interface associated with the program to analyze ratiometric data).

The processing apparatus (block 12), may be, for example, any fixed or mobile computer system (e.g., a personal computer or mini computer). The exact configuration of the computing apparatus is not limiting and essentially any device capable of providing suitable computing capabilities may be used according to the present invention. Further, various peripheral devices, such as a computer display, mouse, keyboard, memory, printer, scanner, complementary metal-oxide-semiconductor active pixel sensor, charge-coupled device, camera, microscope, magnetic resonance imaging apparatus, any imaging apparatus capable of simultaneously or quasi-simultaneously acquiring images at more than one wavelength, etc., are contemplated to be used in combination with processing apparatus (block 12) of the data analysis system (block 14).

In view of the above, it will be readily apparent that the functionality as described in one or more embodiments according to the present invention may be implemented in any manner as would be known to one skilled in the art. As such, the computer language, the computer system, or any other software/hardware which is to be used to implement the present invention shall not be limiting on the scope of the processes or programs (e.g., the functionality provided by such processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information.

FIG. 2 shows a general block diagram of an illustrative data processing method 200 for analyzing ratiometric data according to the present invention. One will recognize that one or more of the blocks of functionality described therein may be carried out using one or more programs or routines.

Generally, the processing method 200 includes providing ratiometric data (block 210) (e.g., a ratiometric dataset representative of image data obtained over time, a ratiometric dataset representative of measurement data obtained over time, etc.). Enhanced ratiometric data may be generated (block 235) using the ratiometric data. In one or more embodiments, such enhanced ratiometric data may then be outputted (block 260) to at least one of, e.g., a user, a display, a printer, and/or a file. Further, the output may be analyzed by a user, used by another machine that provides output based thereon, etc.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus (block 14) described herein.

As described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods according to the present invention, as will be further described herein, may utilize algorithms implementing matrix mathematics (e.g., temporal correlation, spectral correlation, covariance, etc.) to transform the ratiometric data (e.g., a set of ratiometric images taken over time) into enhanced ratiometric data (e.g., a set of enhanced ratiometric images).

FIG. 3 shows a more detailed block diagram of one illustrative embodiment of a method 300 for analyzing ratiometric data as generally illustrated in FIG. 2. The method 300 may be implemented in one or more various manners, some examples of which will be further described herein with reference to FIGS. 4-10B.

One or more ratiometric datasets are provided (block 310) as part of method 300. One or more embodiments of providing a ratiometric dataset are further described in detail with reference to FIGS. 4A & 4B. For example, providing one or more ratiometric datasets may include multiple steps such as, but not limited to, providing datasets (e.g., blocks 411, 412, 1411, & 1412), standardizing datasets (e.g., blocks 413, 414, 1413, & 1414), comparing datasets (e.g., blocks 415 & 1415), and compressing datasets (e.g., blocks 416 & 1416).

Further, in at least one embodiment, each ratiometric dataset may utilize the same experimental stimulus paradigm. For example, each ratiometric dataset may be representative of image data taken over time of different slides of cultured cells prepared the same way.

Still further, the methods and systems according to the present invention may analyze many different types of ratiometric data. For example, the ratiometric data may be fluorescent image data, magnetic resonance image data, differential electrical signal data, image data where, e.g., two wavelengths are simultaneously imaged, and/or other data as would be known by one having ordinary skill in the art.

Also, further, such ratiometric data may be analyzed for one or more objects of interest (i.e., variables of interest) such as, but not limited to, calcium concentrations, membrane potentials, pH using, e.g., Stokes shift dyes (e.g., Di-4,8-Anepps), FRET indicators (e.g., cameleon), combinations of dyes such as Fluo-4/Fura-red where, e.g., one dye increases in emission intensity at one wavelength dependent on the variable of interest and the other dye decreases in emission intensity at another wavelength dependent on the same variable of interest, a combination of an indicator dye that may change its fluorescence depending on changes in a variable of interest and a reference fluorophore, ratiometric dyes where, e.g., two excitation wavelengths are used to generate ratiometric image data, and/or one or more other variables as would be known by one having ordinary skill in the art. The ratiometric image datasets may be provided to the systems and methods of the present invention in the form of any digital file format, container, and/or compression, such as, e.g., a JPEG file, a Bitmap image (BMP) file, MPEG-4 Part 14 container, MPEG-4 Part 10 compression (H.264), an AVI file, etc.

Figure 5:
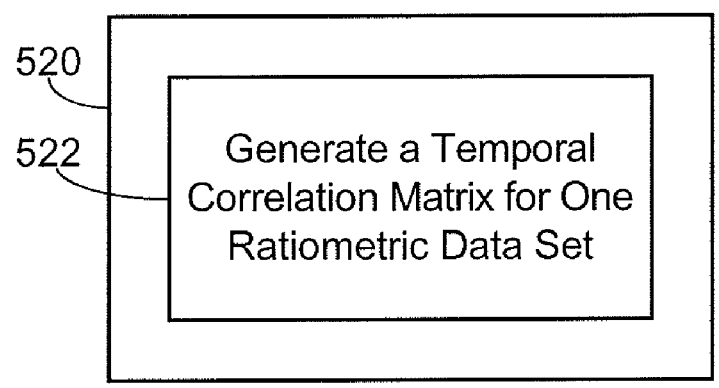
FIG. 5 shows a more detailed block diagram of one illustrative embodiment of a method for generating a correlation matrix for one or more ratiometric datasets as shown generally in the method of FIG. 3.
Figure 6A:
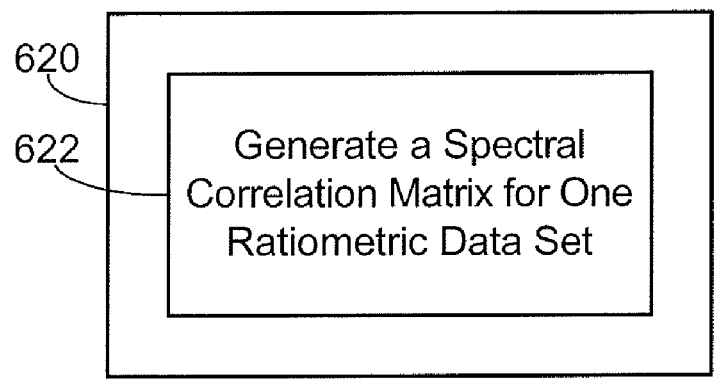
FIG. 6A shows a more detailed block diagram of another illustrative embodiment of a method for generating a correlation matrix for one or more ratiometric datasets as shown generally in the method of FIG. 3.

The method 300 may further include generating a correlation matrix for the one or more ratiometric datasets (block 320). Different types of correlation matrices may be generated (e.g., a temporal correlation matrix as shown in FIG. 5 or spectral correlation matrix as shown in FIG. 6A). One or more embodiments of generating a correlation matrix for the one or more ratiometric datasets are further described in detail with reference to FIGS. 5-8B.

The correlation matrix may be generated from a single ratiometric dataset (e.g., FIGS. 5 & 6A) or two or more ratiometric datasets (e.g., FIGS. 6B-8B). Accordingly, if the method includes two or more ratiometric datasets, the method may further include generating a correlation matrix for each dataset and summing each of the correlation matrices (e.g., blocks 724, 824 & 828) as further described in detail with reference to FIGS. 7-8B.

The method 300 may further include generating a plurality of eigenvalues and plurality of eigenvectors (block 330) from the correlation matrix. The eigenvalues are a statistical measure of the amount of correlation within, for example, a single dataset or, for example, over more than one dataset. One or more embodiments of generating a plurality of eigenvalues and plurality of eigenvectors (block 330) from the correlation matrix are described in further detail below.

The method 300 may further include selecting a set of the eigenvectors from the plurality of eigenvectors (block 340). One or more embodiments of selecting the set of eigenvectors from the plurality of eigenvectors are further described in detail with reference to FIG. 9. Functionally, selecting a set of such eigenvectors may include selecting a set based on a threshold value representative of or determined by, e.g., the expected statistical distribution of the eigenvector pixel values or the projection of the eigenvector in the dataset and/or the user's determination that the eigenvector should be selected.

Using the selected set of eigenvectors and, e.g., the original data, the method 300 may reconstruct a set of enhanced ratiometric data (block 350). One or more embodiments of reconstructing a set of enhanced ratiometric data using the selected set of eigenvectors are further described in detail with reference to FIGS. 10A & 10B.

The enhanced ratiometric data may then be outputted (block 360) to at least one of, e.g., a user, a display, a printer, a file, and/or another computer program for the display or manipulation of the enhanced ratiometric data. In at least one embodiment, the enhanced ratiometric data may be transferred to another system to undergo further processing. For example, a set of enhanced ratiometric fluorescent images of cell cultures may be the input into another process by which the calcium concentrations of cell cultures may be quantitatively analyzed.

Figure 4A:
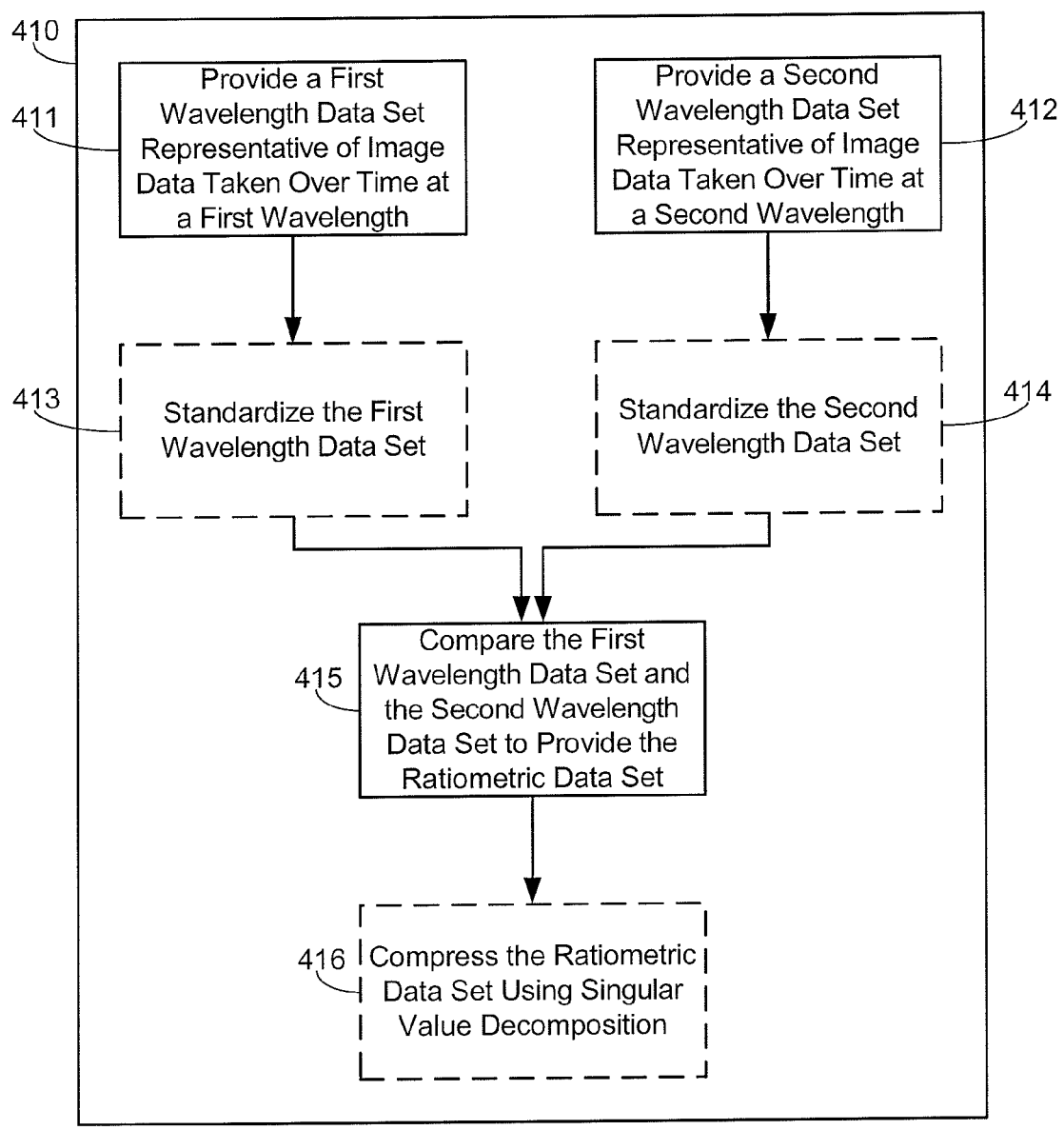
FIG. 4A shows a more detailed block diagram of one illustrative embodiment of a method for providing one or more ratiometric datasets as shown generally in the method of FIG. 3.

One embodiment of a method for providing a ratiometric dataset (block 410) as shown generally in block 310 of the method of FIG. 3 is provided in FIG. 4A. The method (block 410) may generate ratiometric image data from a first and second wavelength dataset taken over time. The method (block 410) may include providing a first wavelength dataset representative of image data taken over time at a first wavelength (block 411) and providing a second wavelength dataset representative of image data taken over time at a second wavelength (block 412). For example, the first wavelength dataset may be taken over the bandwidth of about 515 nanometers (nm) to about 535 nm and the second wavelength dataset may be take over the bandwidth of about 520 nm to about 660 nm.

In one exemplary embodiment, the statistical model for one pixel of a ratiometric signal may be the following:

$$X_1(t) = \alpha b(t)(1-f(t)) + \eta_1(t)$$

$$X_2(t) = \beta b(t)(1-f(t)) + \eta_2(t)$$

$X_{1,2}(t)$ denote time-varying signals in two wavelength bands of a ratiometric signal, which, e.g., may be provided in method 410 in blocks 411 and 412. $\alpha$ and $\beta$ denote scalar multiplicative constants that may be due to differences in the amplitude of the signal at different wavelengths due to filters, etc. Further, for example, in this embodiment, $b(t)$ may denote a multiplicative, time-varying background, for example, accounting for changes in the concentration of fluorophores (e.g., a decrease in fluorophore concentration due to bleaching would be a multiplicative effect) and $f(t)$ may denote an anti-correlated change in the background fluorescence due to a ratiometric, fluorescent indicator (e.g., the signal of interest). The opposite trend in the fluorescence at the two wavelengths (anti-correlation) leads to the minus sign for the $f(t)$ term in the first equation and the plus sign in the second equation. $\eta_1(t) \sim N(0, \alpha\sigma^2)$ and $\eta_2(t) \sim N(0, \beta\sigma^2)$ denote additive white noise in the signal. In typical data, $\alpha$ and $\beta$ are close to being equal. It should be noted that, if one of the f(t)

terms in one of the equations were deleted, the results would still hold. This altered model may represent a second standard way of doing ratiometry, in which one condition independent fluorophore may be used as an internal reference.

A feature of a ratiometric signal is that, in the absence of noise (i.e., $\eta_1(t)=\eta_2(t)=0$), the following ratio $$\frac{X_1(t)}{X_2(t)} = \frac{\alpha}{\beta} \frac{1-f(t)}{1+f(t)}$$

eliminates dependence on the background, b(t), and is solely a function of f(t), the signal of interest. For ratiometric indicators, this ratio may be typically tabulated and quantitative estimates of the concentrations of physiological variables of interest (e.g., voltage, calcium concentration, etc.) may be obtained (see, e.g., K. Truong, A. Sawano, A. Mizuno, H. Hama, K. Tong, T. Mal, A. Miyawaki, and M. Ikura, "FRET-based in vivo $Ca^{2+}$ imaging by a new calmodulin-GFP fusion molecule," Nature Structural Biology 8, 1069-1073 (2001)).

At least in one embodiment, the approach may be to consider the null hypothesis, $\{H_0: f(t)=0\}$. Each of the first wavelength dataset and the second wavelength dataset may optionally be standardized (blocks 413 & 414). For example, the datasets $X_1$ and $X_2$ (e.g., time-varying signals) may be standardized using the following equation:

$$X_i'(t) = \frac{X_i(t) - \overline{X}_i}{\overline{V}_i}$$

where $\overline{X}_i$ denotes the sample mean and $\overline{V}_i$ denotes the sample standard deviation of $X_i$ with i=1, 2. If there is no anti-correlation, the result may provide two time-courses that should lie on top of each other.

According to method 410, the first wavelength dataset and the second wavelength dataset are compared to provide the ratiometric dataset (block 415). Such comparison may be a subtraction. For example, the difference $\epsilon(t) \equiv X'_1(t) - X'_2(t)$ has expectation value $$E\{\epsilon(t)\} = E\{X'_1(t) - X'_2(t)\} = 0$$

and, due to cancellation of the background terms, $\epsilon(t)$ may be the sum of two normally distributed random variables, and, therefore, may be also normally distributed.

After the ratiometric dataset has been provided (block 415), the method (block 410) may optionally compress the ratiometric dataset using singular value decomposition (SVD) (block 416) (e.g., truncated SVD), when, e.g., the number of pixels of the image data is greater than the number of measurements over time. When investigating image data, the number of pixels may probably be greater than the number of measurements over time. For example, the data may be regularized by performing SVD on each dataset, $$\epsilon_j = u_j s_j v_j$$

The number of singular eigenvectors may then be truncated to provide a compressed dataset, $\epsilon_j$, that may respresent a close approximation of $\epsilon_j$. Often, 20 or 30 eigenvectors may be retained. In other embodiments, the number of eigenvectors that may be retained may be, e.g., greater than 10, greater than 20, greater than 30, greater than 50, less than 100, less than 70, less than 50, and/or less than 30 (see, e.g., G. H. Golub and C. F. Van Loan, Matrix Computations, 1996, The Johns Hopkins University Press for a description of the SVD).

As a result, further analysis may be performed on the $v_j$'s instead of the $\epsilon_j$'s, i.e., the further analysis may be performed on the reduced datasets consisting of the $v_j$'s, where there are fewer variables than time points.

In the methods and systems according to the present invention, SVD may be used to compress the data. In other methods (see, e.g., J. Broder, A. Majumder, C. H. Keith, J. D. Lauderdale and A. Sornborger, "Multivariate methods for the analysis of multichannel NADH/Flavoprotein and ratiometric calcium imaging signals," Poster: Program No. 457.9, 2005 Abstract Viewer/Itinerary Planner, Washington, D.C., Society for Neuroscience), SVD is only used to find covarying information. SVD is never used for determining correlation, but only covarying information. In other words, variances and covariances may retain information concerning the amplitude of a time series, whereas all correlations are normalized to be the same amplitude. Therefore, information that might be overlooked in the calculation of covariance due to its low amplitude may be better recognized in the calculation of a correlation.

Figure 4B:
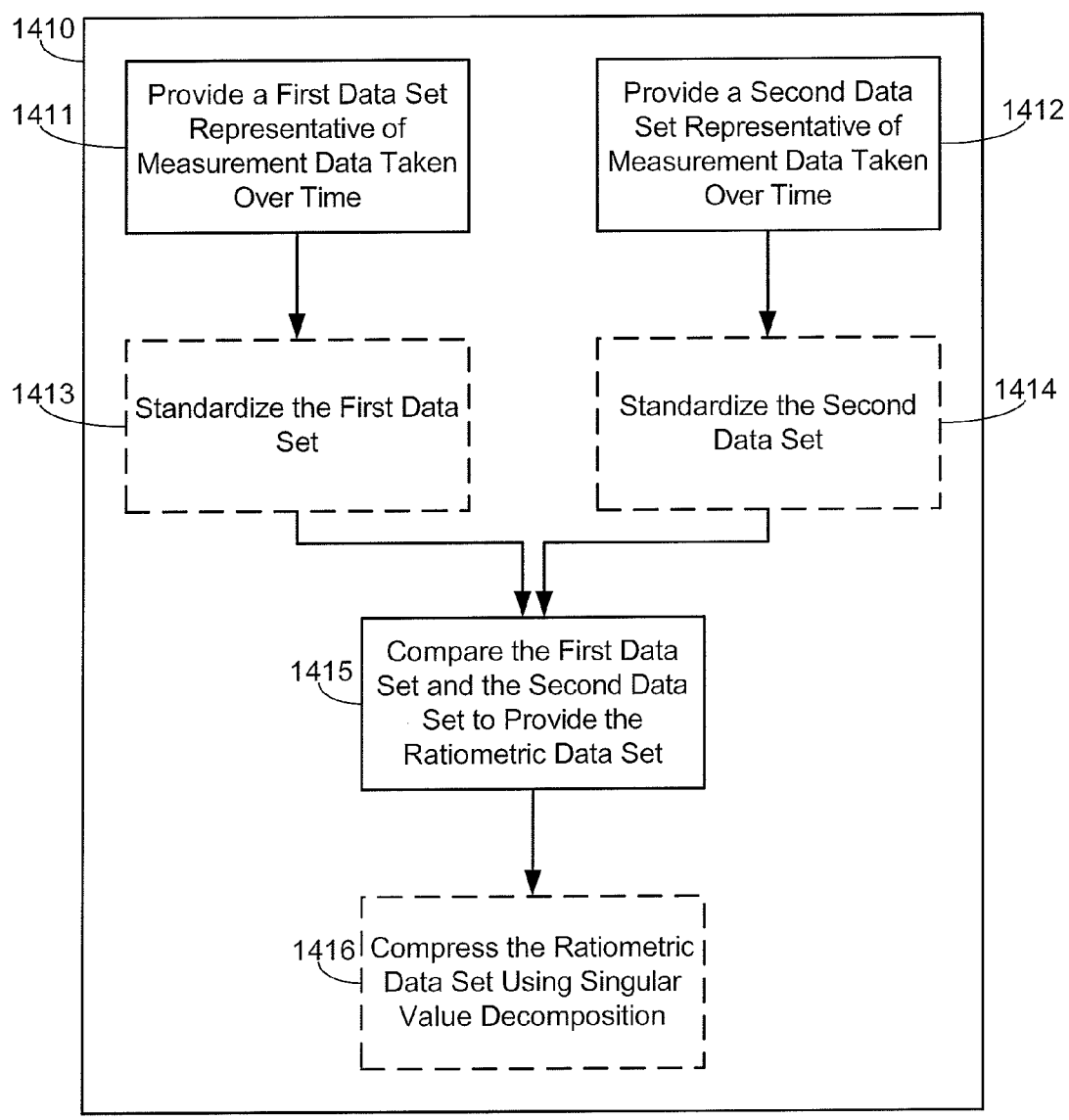
FIG. 4B shows a more detailed block diagram of another illustrative embodiment of a method for providing one or more ratiometric datasets as shown generally in the method of FIG. 3.

Another embodiment of a process for providing a ratiometric dataset (block 1410) as shown generally in the block 310 of the method of FIG. 3 is provided in FIG. 4B. Method (block 1410) provides ratiometric data from a first and second measurement dataset taken over time. The method (block 1410) provides datasets representative of measurement data taken over time (blocks 1411 & 1412) instead of wavelength datasets representative of image data over time as described herein with reference to FIG. 4A. In one or more embodiments, the datasets represent differential measurements over time, e.g., two variables that are expected to diverge in response to the same stimulus over time. In one embodiment, the datasets may be image data. For example, fluo-4 and Fura-Red are both calcium indicators used in fluorescent imaging. The fluorescence of fluo-4 is expected to increase in the presence of calcium while the fluorescence of Fura-Red is expected to decrease in the presence of calcium. The present invention may also be used to analyze other ratiometric image data, such as, e.g., magnetic resonance image data. Further, the present invention may be used to analyze ratiometric data other than image data, such as, e.g., differential electrical signals.

The remainder of the method 1410 may be similar to the method 410 described herein with reference to FIG. 4A. For example, the process steps represented by blocks 1413, 1414, 1415, and 1416 may be substantially similar to the process steps represented by blocks 413, 414, 415, and 416. As such, for simplicity, further description on the details of method 1410 shall not be provided.

The datasets representative of measurement data taken over time may be fluorescent imaging, magnetic resonance imaging, differential electrical signals, and other data as would be known by one having ordinary skill in the art. After comparing the first dataset and the second dataset to provide the ratiometric dataset (block 1415), the method (block 1410) may optionally compress the ratiometric dataset using singular value decomposition (block 1416), when, e.g., the number of variables of the data is greater than the number of measurements over time.

Generally, the remainder of the description herein will address the methods as applied to ratiometric image data. However, such methods, as described herein, may be applied to any other type of ratiometric data.

As described above, one or more ratiometric datasets are provided as shown generally in block 310 of the method 300 of FIG. 3 (e.g., as provided in FIG. 4A). For example, a ratiometric image dataset is provided from a first and second wavelength dataset taken over time. A correlation matrix is generated for the one or more ratiometric datasets (block 320).

One embodiment of generating a correlation matrix for one or more ratiometric datasets (block 520) as shown generally in the block 320 of the method of FIG. 3 is shown in FIG. 5. In this embodiment (block 520), a temporal correlation matrix is generated for a single ratiometric dataset (block 522). For example, the temporal correlation matrix may contain information about similarities in the temporal dynamics of variables (pixels) in the image data.

In one exemplary embodiment of generating a temporal correlation matrix (block 522), under the null hypothesis described herein, for the i'th pixel, $\epsilon_i$ is normally distributed. Therefore, the j'th dataset $\epsilon_j = [\epsilon_{j1}, \epsilon_{j2}, \ldots, \epsilon_{jP}]^T$ is distributed as a P-dimensional, multivariate normal distribution, $\epsilon_j \sim N_P(0, \Sigma)$, where P denotes the number of pixels in the dataset and $^T$ the vector transpose and the distribution has the 0 vector as mean and covariance matrix $\Sigma$.

Images $\Phi_j$ with $j=1, \ldots, n$ that, when projected on their respective datasets $\epsilon_j(t)$, have maximal correlation with some single time-course, Z(t), are desired. Since the formulas may be simpler, the following equations will be written in vector notation instead of matrix notation, i.e., Z(t)=Z, where Z is a row vector with elements the values of Z(t) at the sampled times, $\epsilon_j(t) = \epsilon_j$, where $\epsilon_j$ is a matrix with elements the values of $\epsilon_j(t)$ with columns corresponding to variables and rows corresponding to the sampled times and $\Phi_j = \Phi_j$ where $\Phi$ is a column vector with elements corresponding to the values of the elements of $\Phi$. The correlation (i.e., the correlation matrix for a single ratiometric dataset) between Z and the (vectorized) time-course $\phi_j^T \epsilon_j$ is given by $$r(Z, \phi_j^T, \epsilon_j) = \frac{Z\epsilon_j^T(\epsilon_j\epsilon_j^T)^{-1}\epsilon_j Z^T}{ZZ^T}$$

Figure 7:
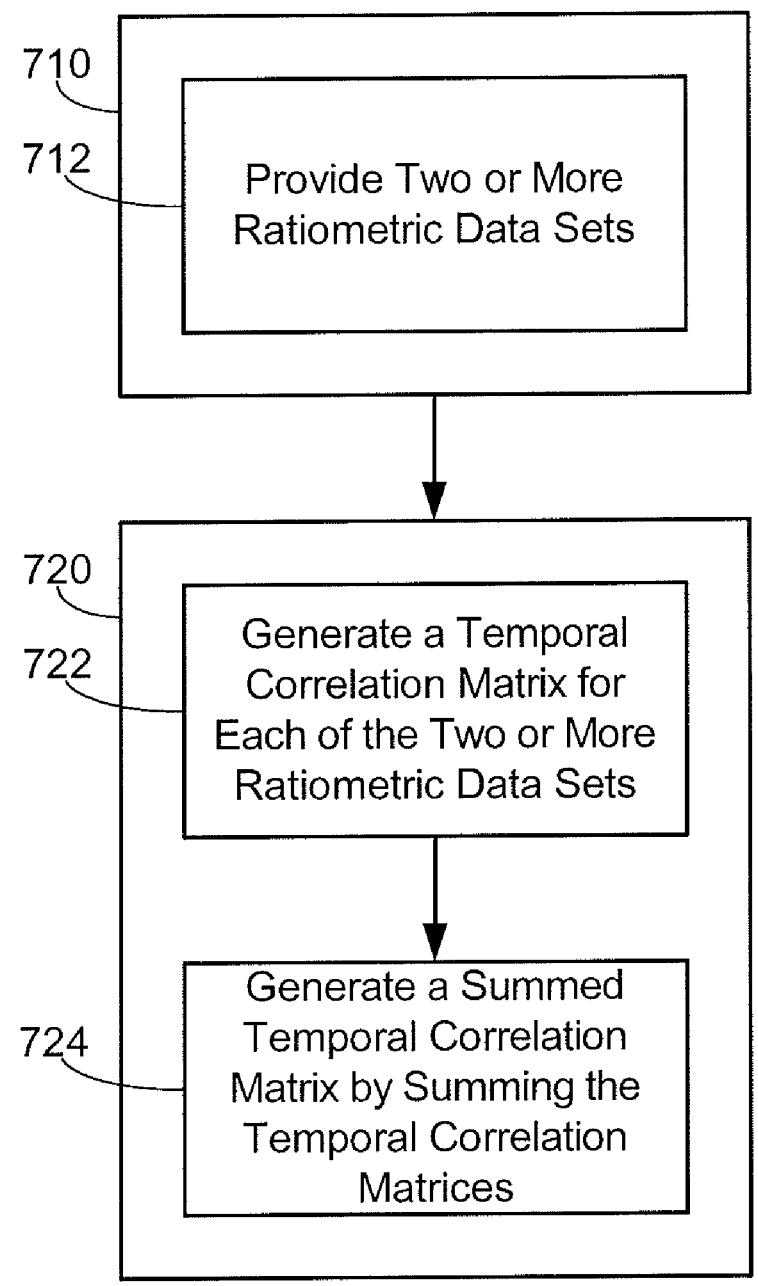
FIG. 7 shows a more detailed block diagram of one illustrative embodiment of a method for providing two or more ratiometric datasets and generating a correlation matrix for the two or more ratiometric datasets as shown generally in the method of FIG. 3.

In one or more embodiments, two or more ratiometric datasets may be provided. In these instances, a temporal correlation matrix may be generated for the two or more ratiometric datasets. One embodiment of generating a correlation matrix for two or more ratiometric datasets (block 720) as shown generally in the block 320 of the method of FIG. 3 is shown in FIG. 7.

In this embodiment, providing a ratiometric data (block 710) may include providing two or more ratiometric datasets (block 712). Since this embodiment utilizes at least two ratiometric datasets, generating a temporal correlation matrix for the two or more datasets (block 720) includes a summation process (block 724). For example, the method (block 720) may include generating a temporal correlation matrix for each of the two or more ratiometric datasets (block 722). The method (block 720) further includes generating a summed temporal correlation matrix by summing the temporal correlation matrices (block 724) that were generated for each of the ratiometric datasets.

In an exemplary embodiment, for example, the correlation (i.e., the temporal correlation matrix) over all datasets becomes $$R^2 = \frac{ZQZ^T}{ZZ^T}$$

where $$Q = \sum_{j=1}^{n} \epsilon_j^T (\epsilon_j \epsilon_j^T)^{-1} \epsilon_j$$

As opposed to generating a temporal correlation matrix (FIGS. 5 & 7), a spectral correlation matrix may be generated for the ratiometric dataset as shown in FIG. 6A. For example, FIG. 6A shows one embodiment (block 620) of generating a spectral correlation matrix for a single dataset (block 622) as shown generally in the block 320 of the method of FIG. 3. In this embodiment (block 620) of the correlation matrix generation method, a spectral correlation matrix is generated for a single ratiometric dataset (block 622). Generally, spectral estimate data may be generated utilizing any spectral estimator such as, e.g., Burg, Covariance, Eigenvector, Modified covariance, Thompson multitaper, Multiple Signal Classification, periodogram, Welch, Yule-Walker, etc.

The spectral correlation matrix may represent the correlation between the spectra of the variables in the image data.

Figure 6B:
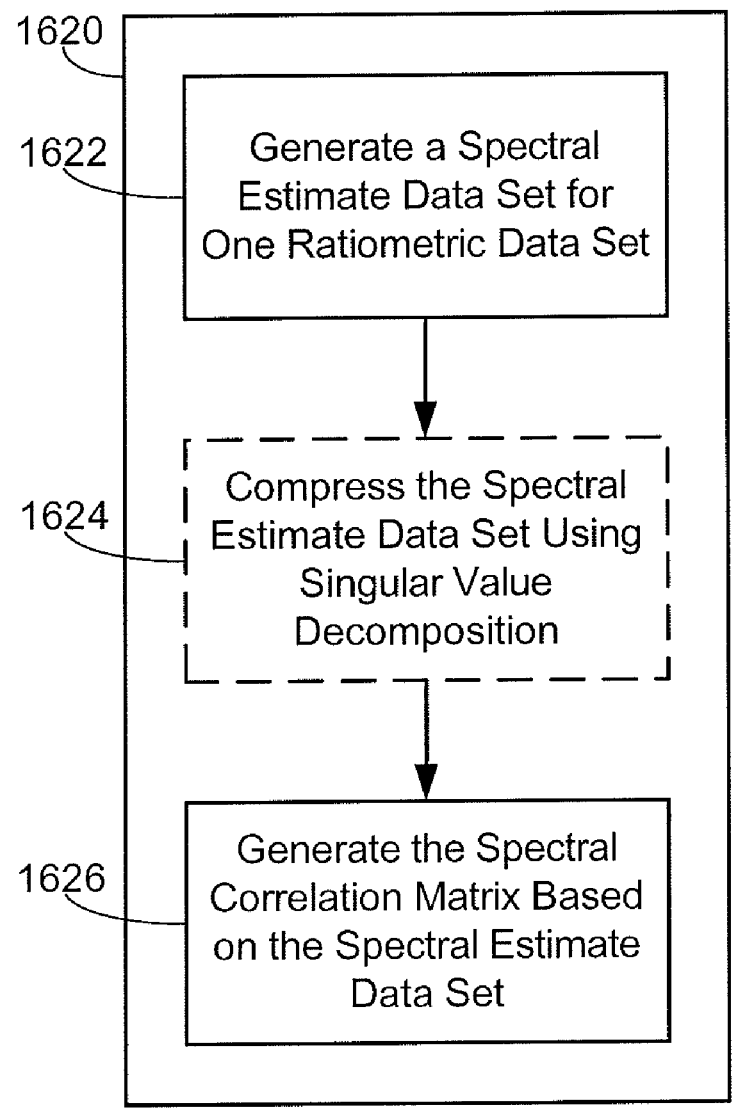
FIG. 6B shows a more detailed block diagram of another illustrative embodiment of a method for generating a correlation matrix for one or more ratiometric datasets as shown generally in the method of FIG. 6A.

Another embodiment of a method (block 1620) of generating a spectral correlation matrix for a single dataset is shown in FIG. 6B. The method (block 1620) includes generating a spectral estimate dataset for a single ratiometric dataset (block 1622) (using, e.g., Thomson's method)

In an exemplary embodiment for generating spectral estimate data, for a realization $X_1, X_2, \ldots, X_N$ of a stationary process $\{X_t\}$ with zero mean the definition is $$\hat{S}_K^{(mt)}(f) = \frac{1}{K}\sum_{k=1}^{K-1}\hat{S}_k^{(mt)}(f) \text{ for } \hat{S}_K^{(mt)}(f) \equiv \Delta t \left|\sum_{t=1}^{N} h_{t,k} X_t e^{-i2\pi f t \Delta t}\right|^2$$

where $\{h_{t,k}\}$ is the kth data taper used. That is, this spectral estimator uses the average of the estimates given by K data tapers. The averaging strategy in general reduces the variance of the final estimate so that as long as bias is not introduced, the computed spectrum may match more closely the actual spectrum of the process. In particular, if the $\hat{S}_K^{(mt)}(f)$ estimates are pairwise uncorrelated then the variance of $\hat{S}_K^{(mt)}(f)$ should be approximately a multiple of 1/K of the variance of any of these individual direct estimates. In order not to introduce bias, the tapers may also be chosen to provide good protection against leakage. These properties of the $\hat{S}_K^{(mt)}(f)$ being approximately uncorrelated and relatively leakage-free follow from the use of data tapers that are approximately uncorrelated with small sidelobes for processes whose spectral density functions have certain properties. As such, the discrete prolate spheroidal sequences (dpss) may be good sequences to use as tapers. A justification for the uncorrelatedness of the $\hat{S}_K^{(mt)}(f)$ for spectra of appropriate type follows from the property (see, e.g., the plots in Percival, Donald B., and Walden, Andrew T. 1993. Spectral Analysis For Physical Applications: Multitaper and Conventional Univariate Techniques. Cambridge University Press, Cambridge, UK, p. 336-338) of the dpss tapers that each successive taper tends to accentuate and attenuate different regions of the data.

As further shown in FIG. 6B, the method (block 1620) may optionally compress the spectral estimate dataset using singular value decomposition represented by block 1624 substantially similar to the compression using singular value decomposition in the process step represented by block 416 as described herein with reference to FIG. 4A. As such, for simplicity, further description on the details of steps represented by block 1624 shall not be provided. The spectral correlation matrix may be generated based on the (compressed or uncompressed) spectral estimate dataset (block 1626).

In one or more embodiments, two or more ratiometric datasets may be provided. In these instances, a spectral correlation matrix may be generated for the two or more ratiometric datasets. One embodiment of generating a spectral correlation matrix for two or more ratiometric datasets (block 820) is shown in FIG. 8A.

Figure 8A:
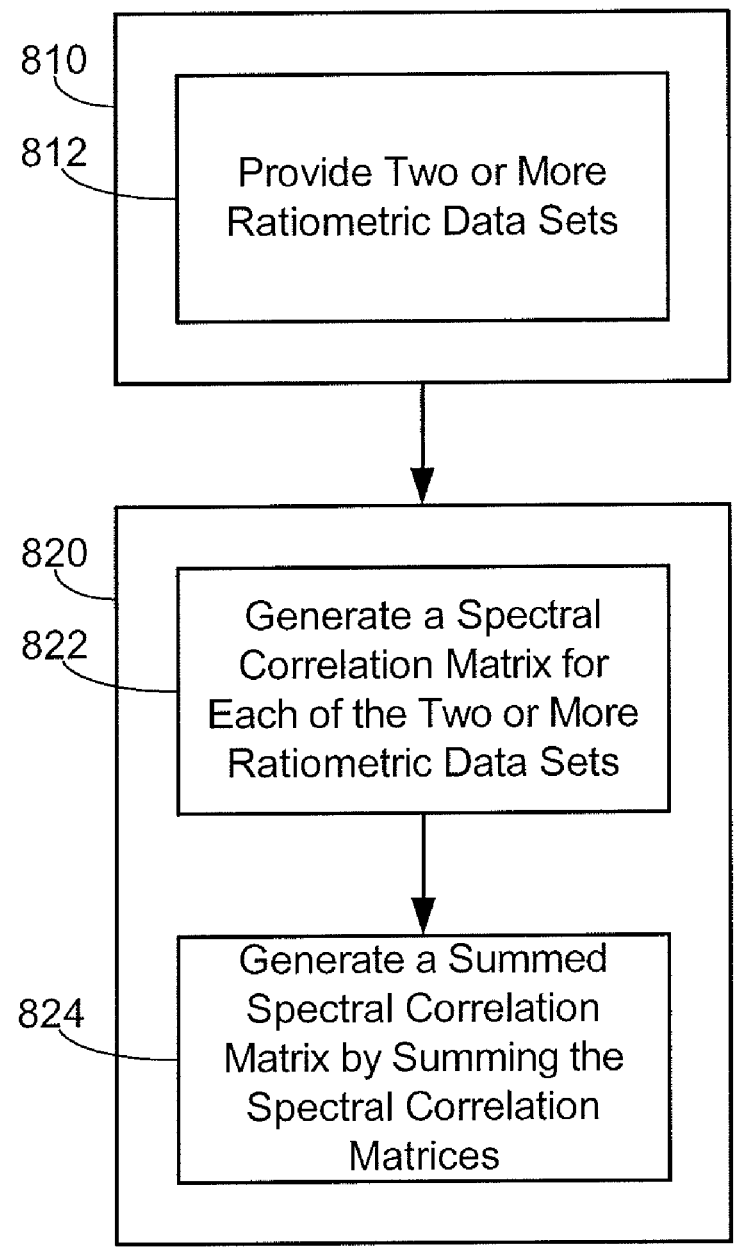
FIG. 8A shows a more detailed block diagram of another illustrative embodiment of a method for providing two or more ratiometric datasets and generating a correlation matrix for the two or more ratiometric datasets as shown generally in the method of FIG. 3.

In this embodiment shown in FIG. 8A, providing ratiometric data (block 810) includes providing two or more ratiometric datasets (block 812). Since this embodiment utilizes at least two ratiometric datasets, generating a spectral correlation matrix for the two or more datasets (block 820) includes a summation process (block 824). For example, the method (block 820) may include generating a spectral correlation matrix for each of the two or more ratiometric datasets (block 822), e.g., as described herein with reference to block 622 of FIG. 6A. The method (block 820) may further include generating a summed spectral correlation matrix by summing the spectral correlation matrices (block 824) that were generated in process step (block 822) as, e.g., described herein with reference to block 724 of FIG. 7.

Figure 8B:
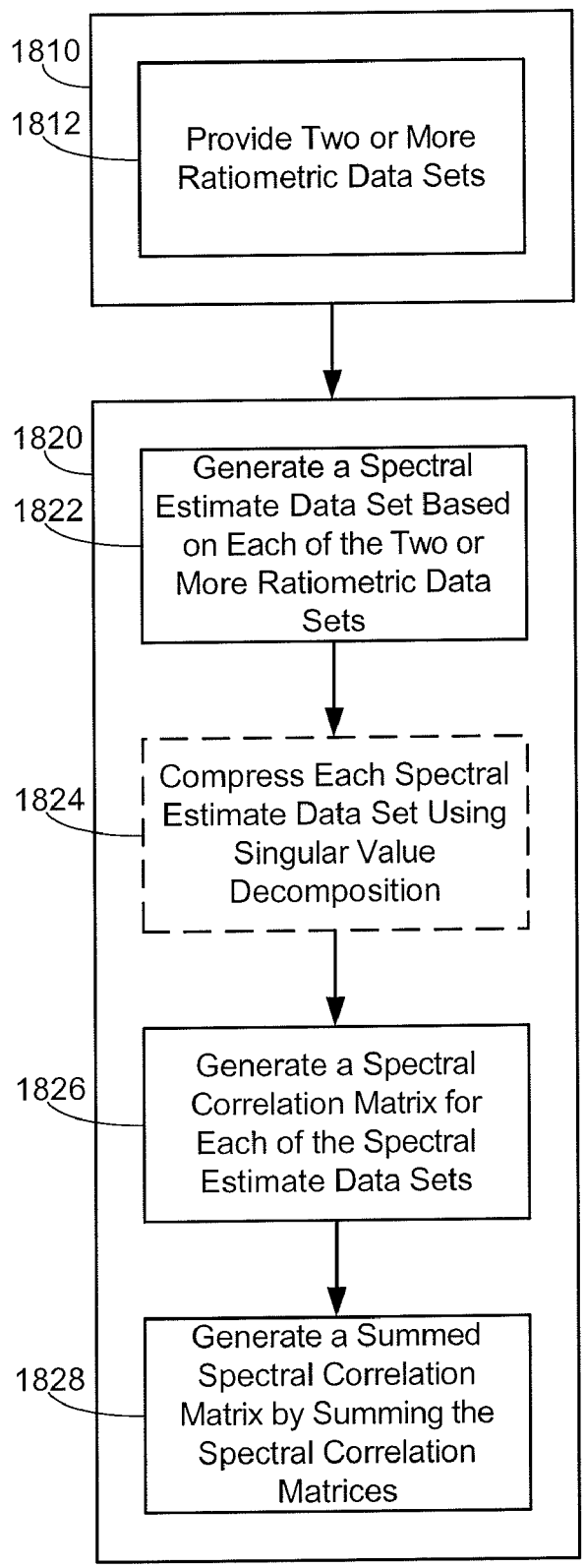
FIG. 8B shows a more detailed block diagram of another illustrative embodiment of a method for providing two or more ratiometric datasets and generating a correlation matrix for the two or more ratiometric datasets as shown generally in the method of FIG. 8A.

Another embodiment of generating a spectral correlation matrix for two or more ratiometric datasets is shown in FIG. 8B. In this embodiment shown in FIG. 8B, providing ratiometric data (block 1810) includes providing two or more ratiometric datasets (block 1812). Since this embodiment utilizes at least two ratiometric datasets, generating a spectral correlation matrix for the two or more datasets (block 1820) includes a summation process (block 1828). For example, the method (block 1820) may include generating a spectral estimate dataset for each of the two or more ratiometric datasets (block 1822), e.g., as described herein with reference to block 622 of FIG. 6A. The method (block 1820) may further include optionally compressing each spectral estimate dataset using singular value decomposition (block 1824) that may be similar to the compression using singular value decomposition in the process step represented by block 416 as described herein with reference to FIG. 4A. The method (block 1820) may further include generating a spectral correlation matrix based on each of the (compressed or uncompressed) spectral estimate datasets. The method (block 1820) may further include generating a summed spectral correlation matrix by summing the spectral correlation matrices (block 1828) that were generated in process step (block 1826), e.g., as described herein with reference to block 724 of FIG. 7.

With reference to FIG. 3, and upon generation of the correlation matrix (block 320), the method 300 may include generating a plurality of eigenvalues and a plurality of eigenvectors based on the correlation matrix (block 330). The correlation matrix (e.g., temporal correlation matrix or spectral correlation matrix) may be provided by, e.g., one of the methods depicted in FIGS. 5-8B.

In one exemplary embodiment of the present invention, it is advantageous to maximize Q, a positive definite or semi-definite matrix. The solution may be given by, $Z_1$, the eigenvector (a time-course in our case) of Q corresponding to the largest eigenvalue that is denoted herein as $R_1^2$. Assuming that $k=1, \ldots, T$ eigenvectors, $\{Z_k\}$, are listed in order of descending eigenvalue, $\{R_k^2\}$ and thus the most significantly correlated time-course will be the first eigenvector, the next most significantly correlated time-course orthogonal to the first will be the second eigenvector, $Z_2$, corresponding to $R_2^2$, etc.

Figure 9:
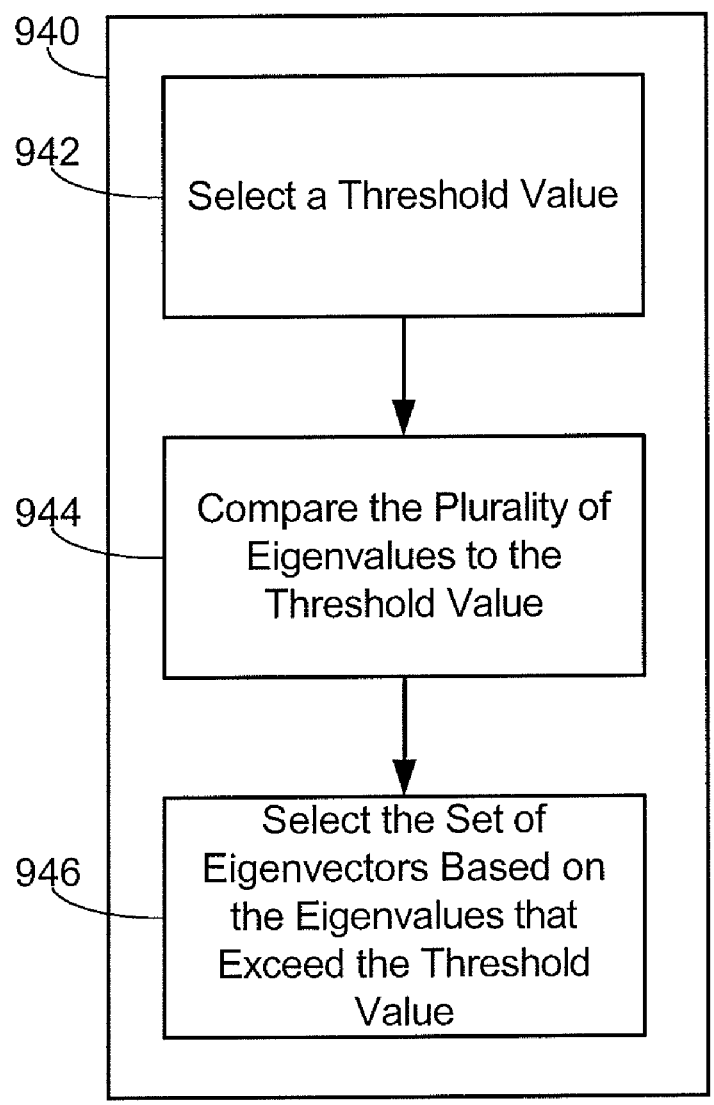
FIG. 9 shows a block diagram of one illustrative embodiment of a method for selecting a set of eigenvectors from the plurality of eigenvectors as shown generally in the method of FIG. 3.

As such, with further reference to FIG. 3, the method 300 may further include selecting a set of the eigenvectors from the plurality of eigenvectors (block 340). One embodiment of selecting the set of eigenvectors from the plurality of eigenvectors (block 940) is shown in FIG. 9. In this selection method (block 940), a threshold value is selected (block 942). The threshold value (e.g., threshold statistical significance for the correlations, $R_k^2$) may be one or more values. In one or more embodiments, the threshold value may be a single value or a defined range of values. For example the threshold value may be the 90th percentile, the 99th percentile and/or any other value as would be known by one having ordinary skill in the art.

The method (block 940) may further include comparing each of the plurality of eigenvalues to the threshold value (block 944). Such comparison may be, e.g., greater than, greater than or equal to, equal to, less than, less than or equal to, any combination of such comparisons, and/or any other comparison as known by one having ordinary skill in the art.

The method (block 940) may further include selecting a set of eigenvectors from the plurality of eigenvectors based on the comparison between the eigenvalues and the threshold value (block 946). In at least one embodiment, a set of eigenvectors from the plurality of eigenvectors is selected based on the eigenvalues (each corresponding to an eigenvector of the plurality of eigenvectors) that exceed the threshold value (block 946).

Setting the statistical significance threshold for acceptance of the eigenvectors as violating the null hypothesis such that all datasets are normally distributed with zero mean and no correlation between datasets may be important in one or more embodiments. One approach may be to set a threshold for $R^2$, as previously described herein, which may be a reasonable procedure if the distribution of the correlations is known. In the classical case of finding correlations only between two datasets, the distribution of the canonical correlations has been calculated (see, e.g., T. Anderson, *An Introduction to Multivariate Statistical Analysis* (John Wiley & Sons, Inc., New York, 1984)). Similar results for multiple datasets, however, have not been published.

Another embodiment of selecting the set of eigenvectors from the plurality of eigenvectors may include selecting the set of eigenvectors based on the correlation coefficient, ρ, of the eigenvectors. For example, a plot of the correlation coefficients, ρ, often has a "knee" at an index where the correlation structure of the eigenvectors changes (e.g., see arrow in FIG. 13A). Other multivariate statistical analyses sometimes use this "knee" to set a threshold. The eigenvector index at the "knee" may be used in principal component analysis to decide where to terminate the expansion.

Still another embodiment of selecting the set of eigenvectors from the plurality of eigenvectors may include testing the eigenvectors for non-normality (e.g., see FIGS. 13B-E). This test is based on the theorem that the marginal distribution of a multivariate normal distribution is yet another, lower dimensional normal distribution. Therefore, the eigenvectors, $\{Z_i\}$ may be normally distributed under the null hypothesis. A standard Lillie test for normality may be used. Used in combination with the correlation coefficient ρ, this procedure may provide an approximation of the location of the desired infonnation in the dataset. This method for calculating statistical significance may be similar to the standard SOARS analysis (see, e.g., J. Broder, A. Majumder, C. H. Keith, J. D. Lauderdale and A. Sornborger, "Multivariate methods for the analysis of multichannel NADH/Flavoprotein and ratiometric calcium imaging signals," Poster: Program No. 457.9, 2005 Abstract Viewer/Itinerary Planner, Washington, D.C., Society for Neuroscience).

Figure 10A:
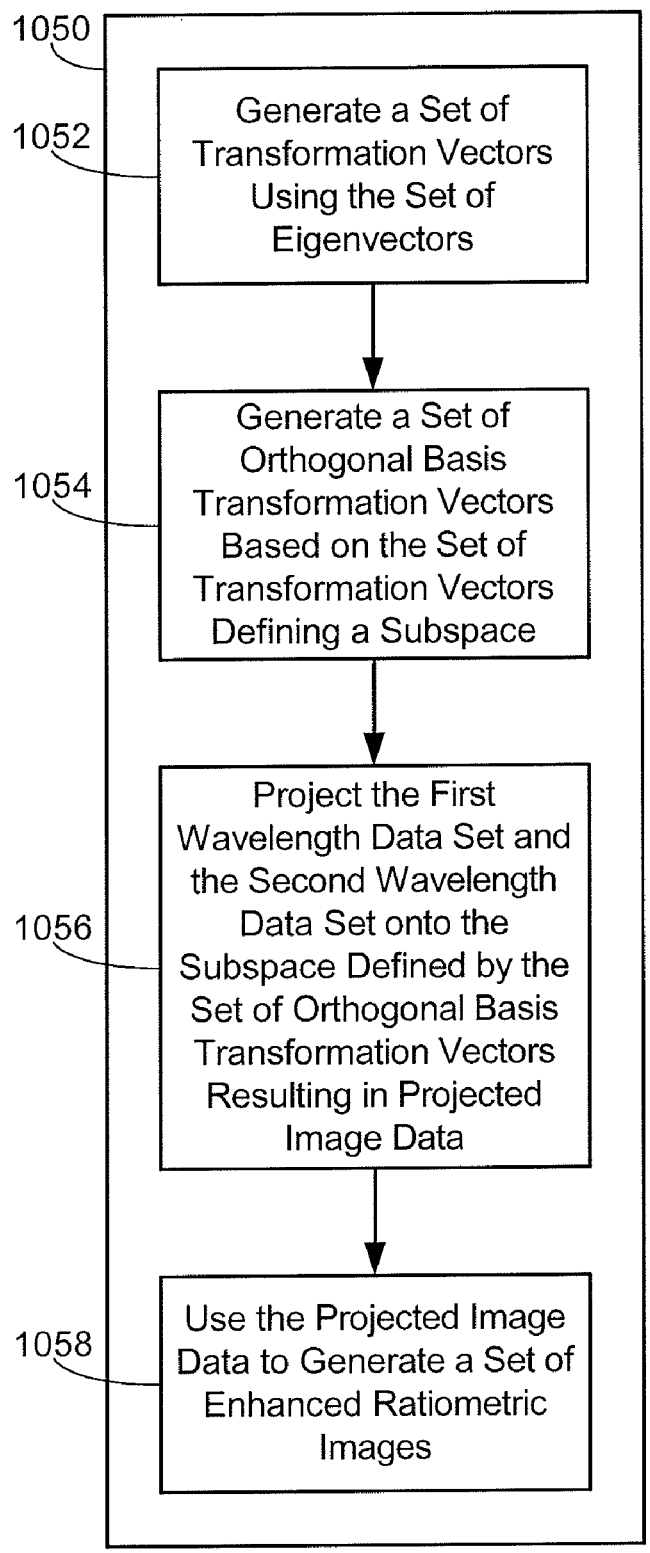
FIG. 10A shows a more detailed block diagram of one illustrative embodiment of a method for reconstructing a set of enhanced ratiometric data using the selected set of eigenvectors as shown generally in the method of FIG. 3.

With further reference to FIG. 3, using the selected set of eigenvectors, the method 300 may reconstruct a set of enhanced ratiometric data (block 350). One embodiment of reconstructing a set of enhanced ratiometric data using the selected set of eigenvectors (block 1050) is shown in FIG. 10A. In this method (block 1050), a set of transformation vectors are generated using the set of eigenvectors (block 1052) (e.g., the set of eigenvectors selected from the plurality of eigenvectors in process step (e.g., block 340 or block 946)).

In an exemplary embodiment, given the time-courses $\{Z_k\}$, the transformation vectors for the j=1, ..., n different datasets $\Phi_j$ are found via the following equation:

$$\Phi_{kj} = Z_k \epsilon_j^T (\epsilon_j \epsilon_j^T)^{-1}$$

The results of this procedure are therefore, 1) a set of eigenvalues, $R_k^2$, 2) a set of time-courses, $Z_k(t)$, 3) a set of images $\Phi_{kj}$ and 4) the projections $\pi_{kj}(t) = \phi_{kj}^T \epsilon_j(t)$, which are the projections of the transformation vectors on their datasets.

The eigenvalues, $R_k^2$, are statistical measures of the amount of correlation between datasets. The time-courses, $Z_k(t)$, represent the part of the projections, $\pi_{kj}(t)$, that is maximally correlated across all j=1, ..., n datasets. The images $\Phi_{kj}$ represent the spatial weights of pixels contributing to the temporal (or spectral) correlation for the j'th dataset and a given statistical significance, $R_k^2$.

The transformation vectors may not be orthogonal vectors. As such, the method (block 1050) may include generating a set of orthogonal basis transformation vectors based on the set of transformation vectors defining a subspace (block 1054). For example, although the transformation vectors may be visualized by reconstructing two-dimensional images from the pixels, to reconstruct a denoised time-series of the spatiotemporal dynamics of the ratio for each dataset, an orthogonal basis may be needed for the images. Therefore, a Gram-Schmidt procedure (see, e.g., Linear Algebra, a Geometric Approach, T. Shifrin and M. Adams, 2002, W. H. Freeman and Co.) may be performed on the statistically significant $\Phi_{kj}$'s giving an orthogonal basis $\{\psi_{ij}\}$ of statistically significant vectors for each of the j=1, ..., n datasets. Using such procedures, e.g., a set of orthogonal basis transformation vectors are generated based on the set of transformation vectors defining a subspace (block 1054).

The method (block 1050) may further include projecting the first wavelength dataset and the second wavelength dataset onto the subspace defined by the set of orthogonal basis transformation vectors resulting in projected image data (block 1056). For example, the $\Phi_j$'s resulting from the above analysis are then projected back into the original space of the images: $\phi'_j = u_j^T \phi_j$.

Each dataset may be projected onto the statistically significant subspace determined by the previously described methods. The original data (i.e., the time-varying signals) may be denoised using the orthogonal basis $\{\psi_{ij}\}$ associated with the statistically significant information by projecting the original data into the subspace defined by the masks $\{\psi_{ij}\}$:

$$X_{j1}^{denoise}(t) := \sum_{i \in R_k^2 > threshold} (\psi_{ij}, X'_{j1}(t)) \psi_i$$

$$X_{j2}^{denoise}(t) := \sum_{i \in R_k^2 > threshold} (\psi_{ij}, X'_{j2}(t)) \psi_i$$

The method (block 1050) may further include generating a set of enhanced ratiometric images using the projected image data (block 1058). Since the original data (e.g., in blocks 413, 414) may have been standardized, the standardization procedure must be inverted in the denoised subspace to form an improved estimate of the ratio $$\mathfrak{R}_{jm}^{estimate}(t) := \frac{\hat{V}_{j1,m} X_{j1,m}^{denoise}(t) + \hat{\bar{X}}_{j1,m}}{\hat{V}_{j2,m} X_{j2,m}^{denoise}(t) + \hat{\bar{X}}_{j2,m}}$$

where $\bar{X}_{ji,m} = \langle X(t)_{ji,m} \rangle_t$ denotes the estimated sample mean from the i'th wavelength band and the m'th pixel in the j'th dataset and similarly for the sample standard deviation $\bar{V}_{ji,m} = \sqrt{\langle (X_{j1,m}(t) - \langle X(t)_{j1,m} \rangle)^2 \rangle_t}$.

Figure 10B:
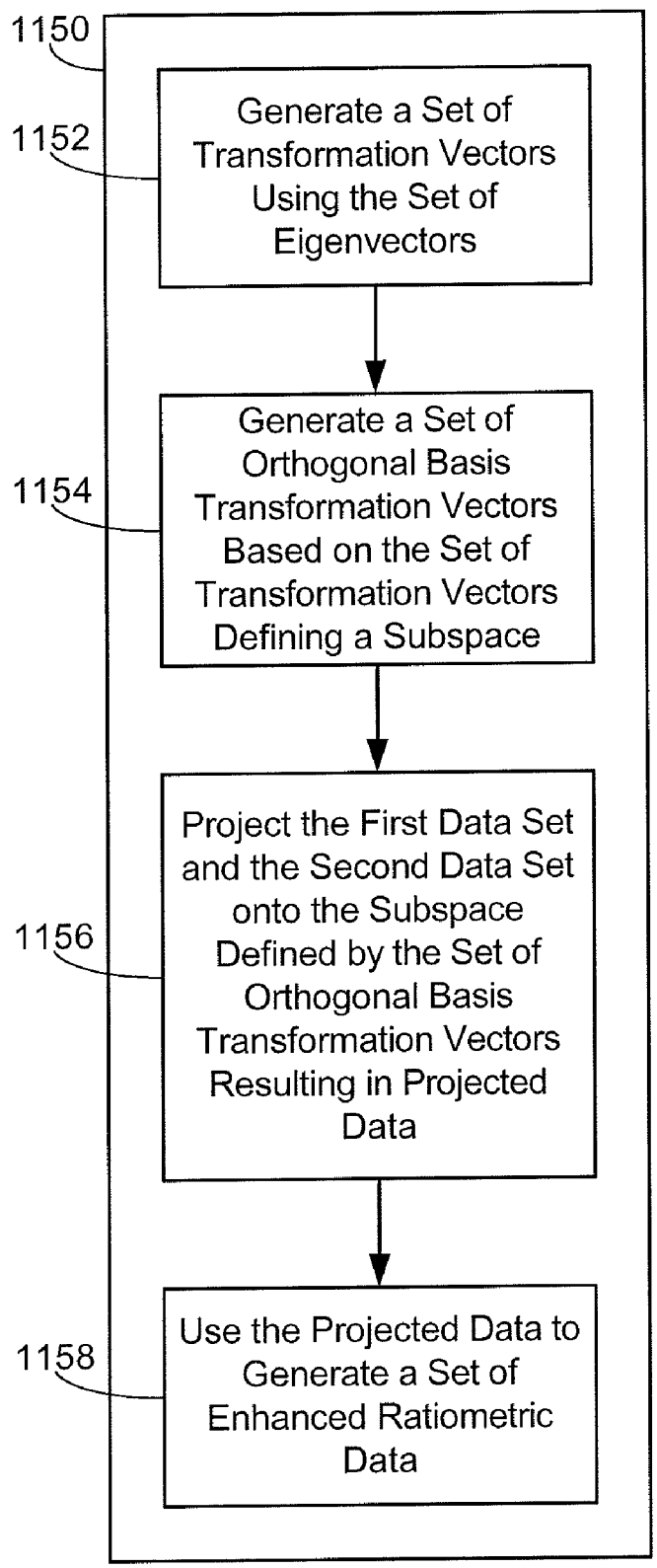
FIG. 10B shows a more detailed block diagram of another illustrative embodiment of a method for reconstructing a set of enhanced ratiometric data using the selected set of eigenvectors as shown generally in the method of FIG. 3.

Another embodiment of reconstructing a set of enhanced ratiometric data using the selected set of eigenvectors (block 1150) is shown in FIG. 10B. In this embodiment, datasets representative of measurement data taken over time are reconstructed instead of wavelength datasets representative of image data over time as described herein with reference to FIG. 10A. The remainder of the method (block 1050) may be similar to the method (block 1150) described herein with reference to FIG. 10A. For example, the process steps represented by blocks 1152, 1154, 1156, and 1158 may be substantially similar to the process steps represented by blocks 1052, 1054, 1056, and 1058 described herein with reference to FIG. 10A. As such, for simplicity, further description of the details of method 1150 shall not be provided.

Some extra information in the ensemble of datasets from the analysis may exist that may be advantageous. In a group of datasets, there may often be variability in the response to a stimulus from one dataset to another. To assay the variability in the response, the correlation coefficient may be calculated between the projections $\pi_j$ and the canonical time-course, $Z(t)$ (see, e.g., Papoulis, A. and Pillai, S. U. "Probability, Random Variables and Stochastic Processes," McGraw-Hill, 2002). If some of the j=1, ..., n datasets are clearly not responding, such datasets may be eliminated (basically a generalized masking procedure) and the whole analysis may be repeated. In the repeated analysis, fewer datasets that respond better to the stimulus may be analyzed and a less noisy representation of the response to stimulus would be expected.

EXAMPLE

Use of Present Invention to Enhance Ratiometric Data Based on Fluoroescent Images The following provides examples of the use of methods and systems according to the present invention.

Experimental Setup

Cultured PC12 cells on 25 millimeter (mm) circular cover glasses were bulk loaded immediately before imaging with 1 µM fluo-4 (Invitrogen/Molecular Probes, Eugene, Oreg. F14217) and 10 (block M Fura-Red (Invitrogen/Molecular Probes, F3021) acetoxymethyl (AM) ester fluorescent indicator dyes in Hanks balanced salt solution (HBSS) (see J. Hanks, "Hanks' balanced salt solution and pH control," Tissue Culture Association Manual 3, 3-5 (1976)), 0.04% Pluronic F-127 (Invitrogen/Molecular Probes, P6867) for 20 minutes at room temperature. After loading, the cells were rinsed with HBSS and mounted in a Dvorak-Stotler chamber (Lucas-Highland, Chantilly, Va.). The cells were periodically stimulated (2 minutes off/2 minutes on) for ten periods (40 minutes total) followed by 5 minutes of perfusion with a control solution of ionomycin+EGTA (low calcium clamp) to reduce calcium to base levels, followed by 5 minutes of perfusion with ionomycin+10 mM $Ca^{++}$. Fluorescence and optical images were acquired with a Leica SP2 confocal microscope on a DM RXE upright microscope platform (Leica Microsystems, Bannerbrook, Ill.) at a frame rate of 1 Hz. 256×256 pixel images (1 μm per pixel) were taken of cultured PC12 cells and their neurites. Due to computational memory limitations, images were subsequently binned to 128×128 pixels. Fluo-4 and Fura-Red were both excited at 488 nm. Simultaneous images were acquired in three bands: 515-535 nm for fluo-4 fluorescence emission, 620-660 nm for Fura-Red fluorescence emission, and transillumination images were taken to detect any motion by the cells.

Cell Culture

PC12 cells (American Type Culture Collection, Bethesda, Md.) were routinely cultured on tissue culture dishes coated with 0.1 mg/ml rat tail collagen (Sigma Chemical, St. Louis, Mo.). Cells were cultured in RPMI 1640 (Sigma Chemicals, St. Louis, Mo.) supplemented with 10% horse serum (JRH Biosciences, Lenexa, Kans.) and 5% Fetal Bovine Serum (FBS) (Atlanta Biologicals, Atlanta, Ga.). For experiments, cells were plated on 25 mm circular cover glasses (Fisher Scientific, Atlanta, Ga.) that had been coated with 0.7% polyethyleneimine (Murnane et al., 2002), and post-coated with collagen. Before each experiment these cells were differentiated for 5 days in RPMI 1640 supplemented with 4% horse serum, 2% FBS, and 100 ng/ml of 7S NGF (Grade 2, Alomone Laboratories, Jerusalem, Israel.)

Results from Simulated Data

Four, dual-wavelength datasets of simulated ratiometric data were generated. Each dual-wavelength dataset consisted of four, two-dimensional Gaussian functions, $G_i(x, y)$ with $i \in 1, \ldots, 4$, with varying length principal axes. The time-course, $T_i(t)$, of each of the Gaussian functions varied in the same way that would be expected for ratiometric data, i.e., when the time-course increased at one wavelength, it had a corresponding decrease at the other wavelength. An overall background, B, was added to the simulated data. Normally distributed noise with the same standard deviation at both wavelengths, $\mu_{1,2}(t)$, was added to each pixel time-course. Thus, the four simultaneous ratiometric signals plus noise combined to make simulated datasets at two wavelengths, $$X_1(x, y, t) = B + \sum_{i=1}^{4} G_i(x, y)T_i(t) + \eta_1(t)$$

$$X_2(x, y, t) = B - \sum_{i=1}^{4} G_i(x, y)T_i(t) + \eta_2(t)$$

The datasets, $X_1$ and $X_2$, were then mean subtracted and standardized as described herein to give $\epsilon_1(t)$. A similar procedure was applied to all four dual-wavelength datasets, resulting in four mean-subtracted, standardized datasets, $\epsilon_1$, $\epsilon_2$, $\epsilon_3$, and $\epsilon_4$. In each of these datasets, there was a single temporally correlated region of activity of similar size and time-course. The other regions were randomly located with different sizes, temporal frequencies and phases.

Figure 11:
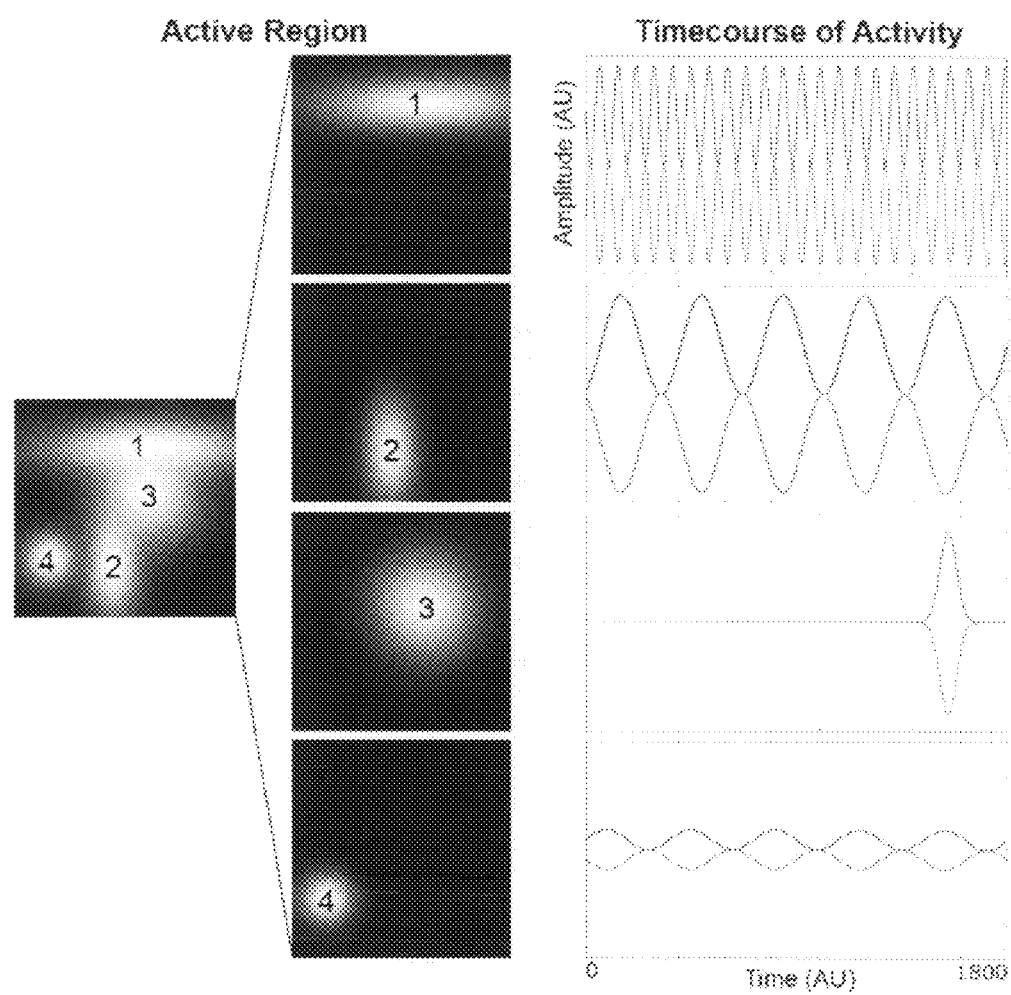
FIG. 11 shows representations of a set of Gaussian functions along with their respective time-courses at each of the dual wavelengths for use in describing an example.

In FIG. 11, a representative set of two-dimensional Gaussian functions are plotted along with their time-courses at each of the dual wavelengths, which is a simulation of a brain region with four spatiotemporally distinct regions of activity. Each region of activity is represented by a bright area (Gaussian profile) with corresponding time-courses at two wavelengths. The intensity at one wavelength increases in response to activity, while at the other wavelength the intensity decreases in response to the same activity.

The activity in regions 1, 2 and 4 represents sinusoidal responses at different frequencies. Of the three sinusoidal time-courses, the one associated with region of activity 4 had one-fifth the amplitude of the others, but was exactly the same for each of the four dual-wavelength datasets. Active region 3 represents an isolated event (i.e., a temporal Gaussian function). These regions of activity are combined to form one simulated image dataset. Low amplitude, normally distributed noise was added to the dataset. This dataset represents simulated activity in a single brain. The methods according to the present invention may be designed to analyze any number of such datasets at the same time (e.g., one dataset, two or more datasets, ten or more datasets, etc.).

Figure 12:
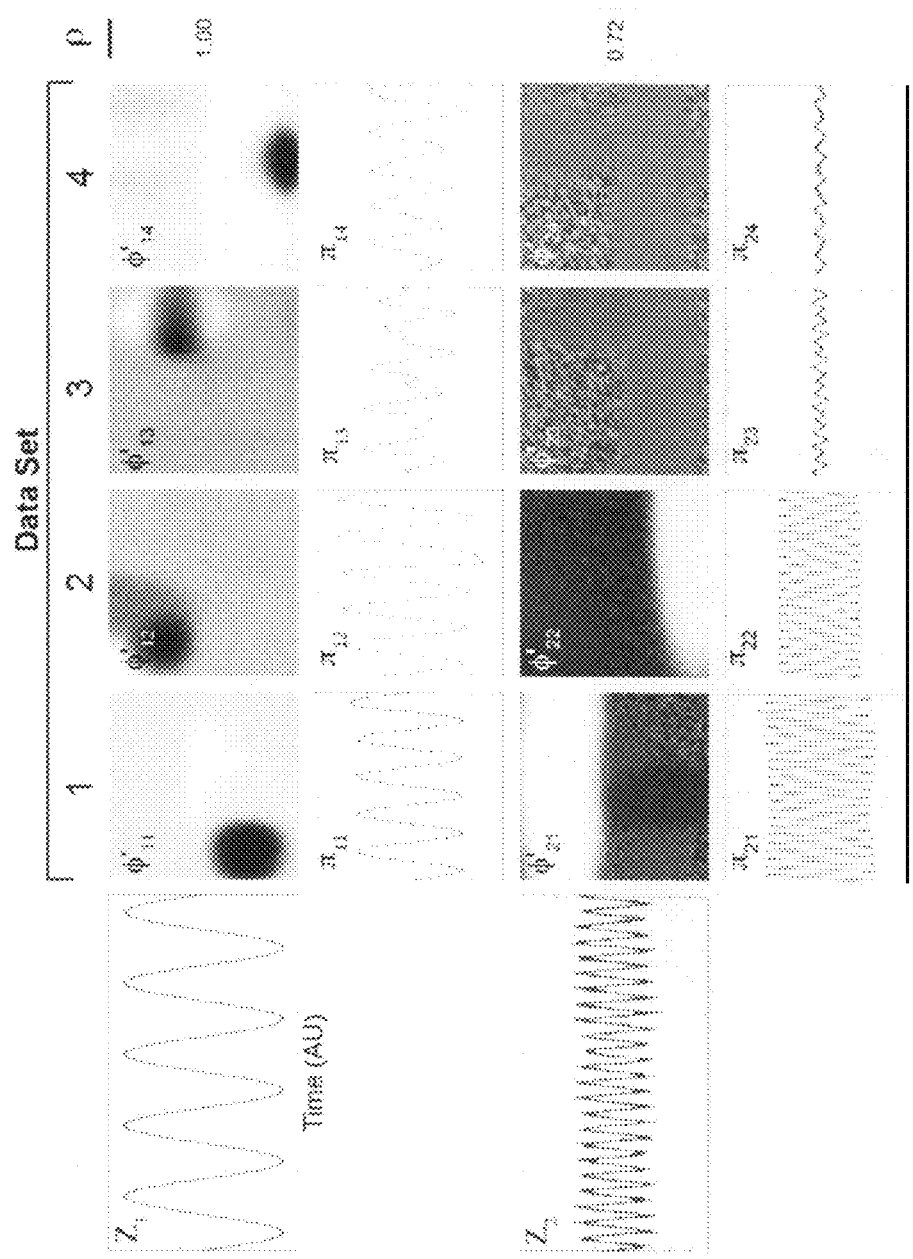
FIG. 12 shows the results utilizing the methods according to the present invention on the data provided in FIG. 11 for use in describing an example.

Some results of applying the methods described herein are plotted in FIG. 12. The four simulated ratiometric image datasets of the type depicted in FIG. 11 were analyzed using the methods and systems according to the present invention. Dataset 1 in this figure is the dataset depicted in FIG. 11. In each of these datasets, there was a single temporally correlated region of activity of similar size and time-course of the inactive region 4 in FIG. 11. The other regions of activity had randomly assigned sizes, locations and time-courses. In the leftmost column, the first two eigenvectors $Z_1$ and $Z_2$ are presented. In the rows to the right of the eigenvectors, their associated transformation vectors $\phi'_{11,12,13,14}$ and $\phi'_{21,22,23,24}$ are depicted. Below the transformation vectors, the projections, $\pi_{11,12,13,14}$ and $\pi_{21,22,23,24}$ are depicted.

The main thing to note here is that, although there were three other larger sources of variance, eigenvector $Z_1$ faithfully captures the sinusoid of FIG. 11, active region 4. Its correlation coefficient $\rho_1=1.00$ implies that this time-course was very correlated among all datasets. $\phi'_{11}$ captures the signal size and location of the active region well. The other transformation vectors capture the size and location of the corresponding active regions in their respective datasets. The projections $\{\pi_{ij}\}$ show how well each transformation vector is able to isolate the correlated activity. For instance, the active region represented by $\phi'_{11}$ was spatially isolated from other active regions. Therefore, its time-course, $\pi_{11}$, is very close to $Z_1$. However, the active region represented by $\phi'_{13}$ overlapped another (uncorrelated) active region. Therefore, $\pi_{13}$, includes some superimposed temporal activity. The other projections have more or less similar characteristics. Eigenvector $Z_2$ represents less correlation among the datasets. Because the uncorrelated active regions had randomly assigned frequencies and phases, there was some accidental correlation among the datasets. This accidental correlation was captured in $Z_2$ and its transformation vectors and projections.

Figure 13:
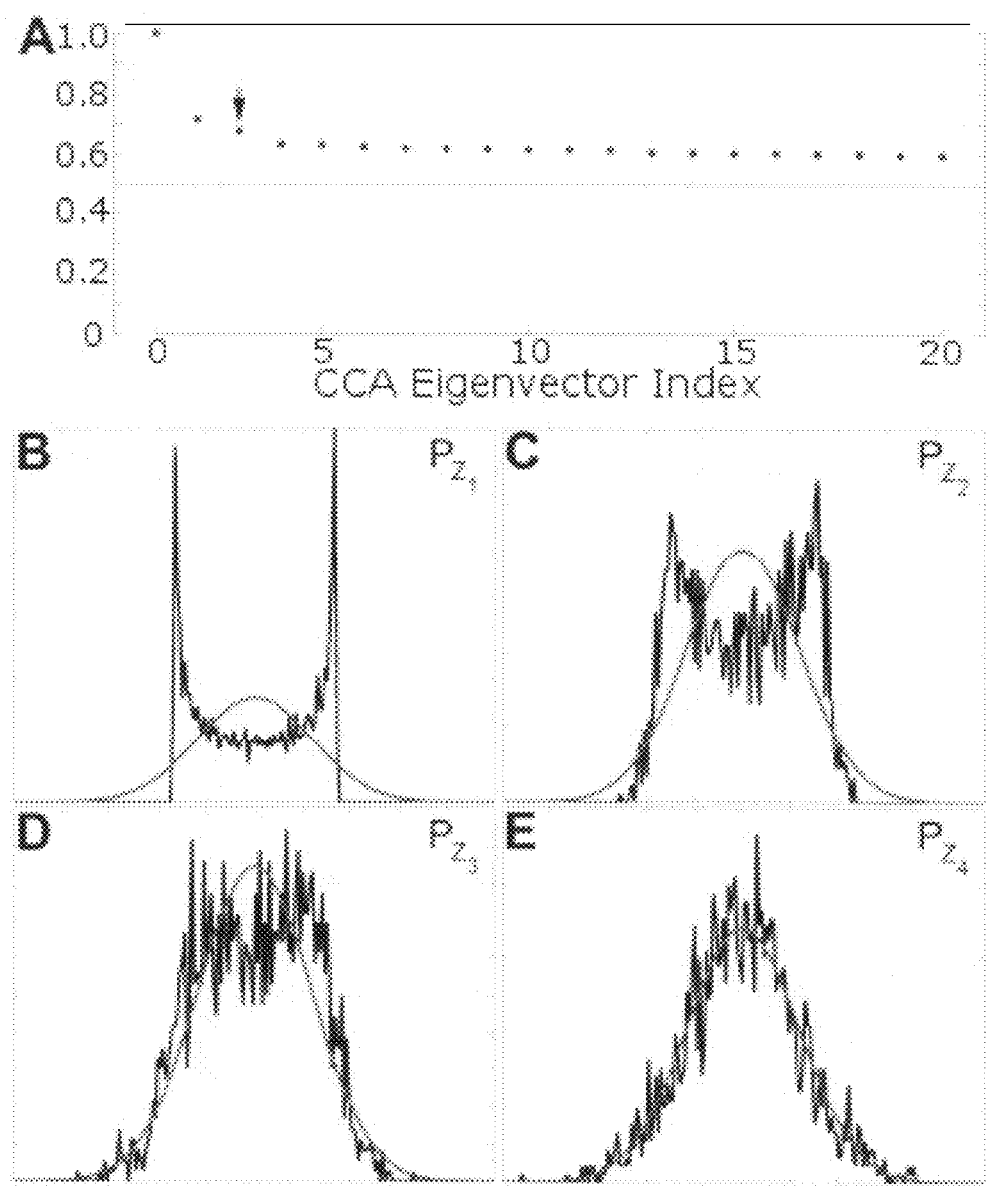
FIG. 13 shows graphical representations utilized for the determination of the statistical threshold utilizing the methods according to the present invention on the datasets provided in FIG. 11 for use in describing an example.

In FIG. 13, the details of the determination of the statistical threshold according to the present invention are shown on the four simulated datasets. In Graph A, $\rho$ is plotted for the first 20 eigenvectors. Note the "knee" in the distribution of $\rho$'s (an arrow shows the location of the "knee," which represents the location of an abrupt change in the correlations). Histograms B, C, D, and E show the probability distributions of the first four eigenvectors, $P_{z_{1,2,3,4}}$ with superimposed normal distributions. Note that the normal distribution is approached as the index increases. Lillie tests for normality show that the first three eigenvectors are non-normally distributed with 99% confidence, whereas the fourth (and all subsequent eigenvectors) are normally distributed. Therefore, only the first three eigenvectors are retained to reconstruct estimates of the ratio.

Results from Experimental Data

Eight datasets obtained from calcium imaging experiments of differentiated PC12 cells bulk-loaded with fluo-4 and Fura-red were analyzed. These datasets were chosen to illustrate the capabilities of the present invention in the presence of variable responses in the data. Datasets 1, 5 and 6 were measurements in which dye loading and the responses are representative of successful experiments. Dataset 2 was an experiment where fluorescent debris disrupted the measurements late in the experiment. Datasets 3 and 7 were experiments with a three-fifths reduction in stimulus concentration. Dataset 8 was expected to be successful, but for some reason was not. Dataset 4 was a control in which the stimulating solution was replaced with a non-stimulating solution. The first and fifth datasets were previously analyzed (see, e.g., J. Broder, A. Majumder, C. H. Keith, J. D. Lauderdale and A. Sornborger, "Multivariate methods for the analysis of multi-channel NADH/Flavoprotein and ratiometric calcium imaging signals," Poster: Program No. 457.9, 2005 Abstract Viewer/Itinerary Planner, Washington, D.C., Society for Neuroscience).

Figure 14:
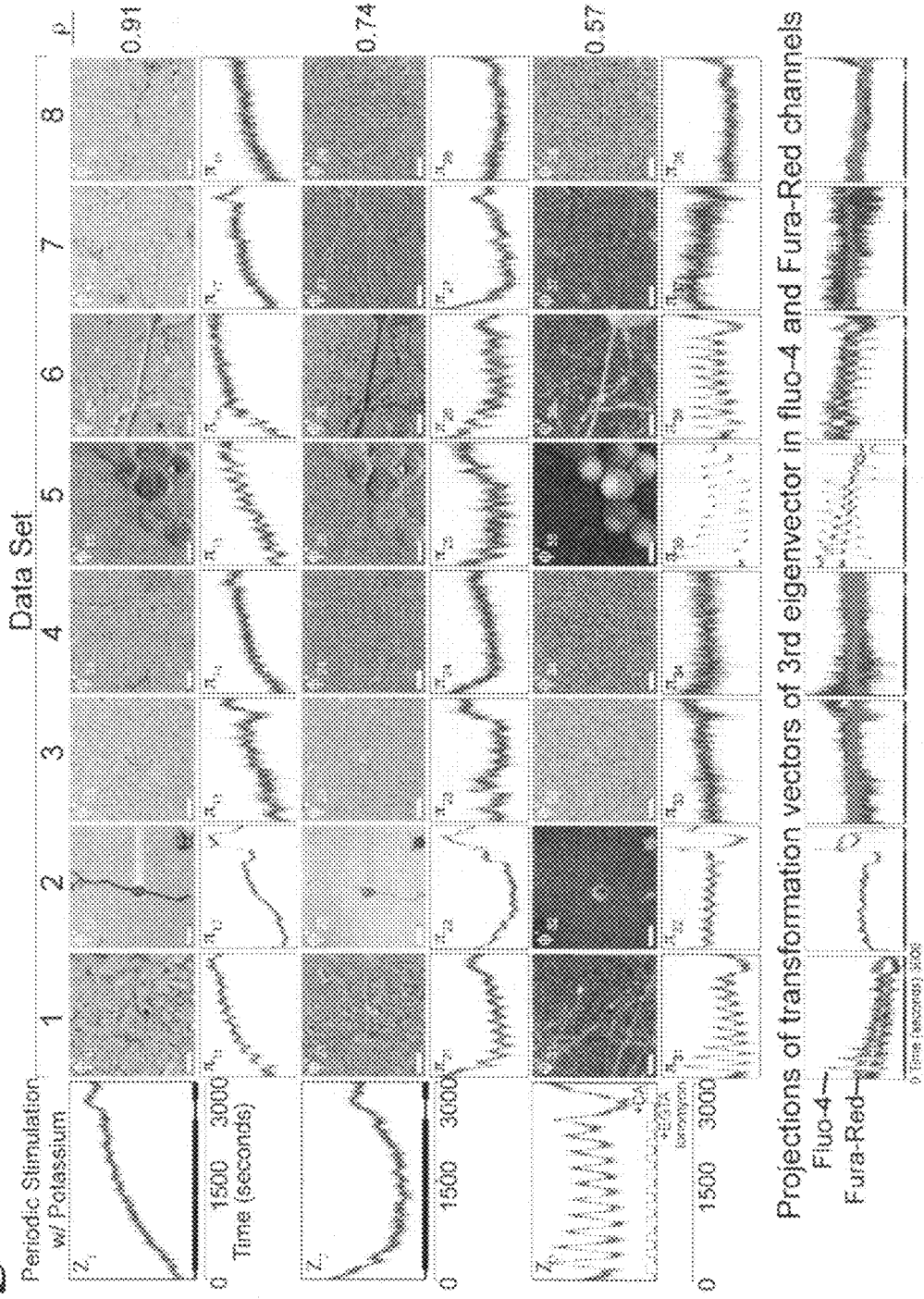
FIG. 14 depicts representations of eigenvectors, transformation vectors, and projections of the transformation vectors into standardized datasets of ratiometric fluorescent image data for use in describing an example.

The eigenvectors, $\{Z_i\}$, of the pooled correlation matrix, Q, are plotted in FIG. 14 in the leftmost column. In the subsequent columns of FIG. 14, the transformation vectors, $\{\phi'_{ij}\}$ (associated with the eigenvector of the row), and their projections, $\{\pi_{ij}\}$, are plotted for the first three eigenvectors. In the bottom-most row, the projections of the transformation vectors of the third eigenvector in the standardized datasets at the fluo-4 and Fura-red emission wavelengths are plotted. Plotting these projections may visualize how well the methods of the present invention are able to identify anti-correlated information in the datasets. In the rightmost column, the statistical significance, $$\rho = \sqrt{\frac{1}{8}R^2}$$

with i∈1,2,3, is plotted for each eigenvector.

Many inferences may be drawn from the results in FIG. 14. First, because $Z_3$ exhibits the highest correlation with the stimulation paradigm, $Z_3$ probably represents a significant part of the response to stimulation. The second inference that may be drawn is that datasets 3, 4, 7 and 8 represent experiments in which the PC12 cells did not respond significantly to periodic stimulation, but 1, 2, 5 and 6 represent experiments in which the cells responded. The average correlation of $\pi_{33,34,37,38}$ with $Z_3$ is 0.21, whereas the average correlation of $\pi_{31,32,35,36}$ with $Z_3$ is 0.76. The third inference that may be drawn is that $Z_1$ and $Z_2$ are likely to represent systematic artifacts in the experiment that occurred across all datasets. Such artifacts might include fluorescence changes from differential bleaching between the fluo-4 and Fura-red fluorophores or other systematic changes over the course of the imaging experiment. That $Z_1$ and $Z_2$ are artifacts may be seen from the fact that all projections $\pi_{1j}$ and $\pi_{2j}$ with j∈1, . . . 8 exhibit a significant positive correlation with $Z_1$ and $Z_2$ (respectively) even though some of these datasets do not respond to the stimulus (e.g., the control). Although some oscillations from the stimulus are visible in $\pi_{11,12,15,16}$ and $\pi_{21,22,25,26}$, remember that the $\phi'_{ij}$'s are not orthogonal between different i's, therefore some oscillations from the stimulus are visible in $Z_1$ and $Z_2$, but do not contribute to correlations with the $Z_i$'s. The large $\rho$ values for $Z_1$ and $Z_2$ are understandable, since a systematic artifact across all datasets is expected to appear with a large correlation. The results in FIG. 14 show that the use of the present invention along with extra information concerning our stimulus paradigm has allowed us to identify $Z_3$ as an eigenvector associated with physiological phenomena in our data.

Once the eigenvectors that capture physiologically relevant information have been selected, the denoised ratio is reconstructed using the projections of the ψ's on the standardized fluo-4 and Fura-red measurements. In the bottom row of FIG. 14, the projections of Φ (a vector in the space of the ψ's ) for the third eigenvector are plotted. Although there is divergence in all of the projections, only those datasets identified herein as responding to the stimulus exhibit large anti-correlations. Although not included in the FIG. 14, $Z_4$ also contained some features of the stimulus protocol, and had a correlation coefficient of 0.53. However, subsequent eigenvectors had correlation coefficients of less than 0.5 and were therefore not significant.

Discussion of the Results from the Simulated and Experimental Data

The present invention may result in a significant improvement in the statistical detection and estimation of ratiometric signals. The present invention provides statistical measures for the selection of relevant eigenvectors, which may provide users with less subjective, user-dependent methods (e.g., an example of a subject, user-dependent methods may be calculating average ratios over regions of interest). Further, the present invention provides methods to automate the analysis of many datasets, thereby increasing the amount of useful data that may be analyzed and the sensitivity of detection of potentially important responses.

One use of the present invention may be the estimation of neural activity in the intact brain. Background neural activity can be a significant confound when an investigator is trying to determine the neural response to a stimulus. The dataset with large amplitude confounding signals in the simulated results section shows that the methods according to the present invention may be very effective at identifying correlated activity. The simulated results also may show that the methods according to the present invention are to "pick out" the neural activity associated with the stimulus protocol, and thus may provide a means for the estimation of stimulus-evoked neural activity in complex environments such as the intact brain.

The methods according to the present invention may rank all statistically significant correlation in a single or multiple datasets, which allows the selection of statistically significant eigenvectors (and their transformation vectors) representing correlations between the datasets. However, it is not necessarily true that an individual eigenvector may capture a single physiological process. As shown in the experimental results section, eigenvectors $Z_1$ and $Z_2$ in FIG. 15 contained correlated information that was very likely due to a systematic artifact. This artifact may have been an aspect of the physiology, due to differential bleaching, or an unknown factor. Through a set of inferences based on our stimulus protocol, $Z_3$ may be identified as best representing a physiologically meaningful response. The remainder of the response appears to have been captured by $Z_4$. The fact that the physiological response and the artifact separated into two distinct groups of eigenvectors may have been due to their independence, which may not necessarily always be the case. If an artifact is partially correlated with a physiological response, a mixing of the eigenvectors that represent those aspects of the signal is expected. Nevertheless, the present invention may still provide meaningful information concerning ratiometric signals in the data that would be difficult to detect with other means.

In the experimental results section, the present invention provided a detailed overview of the response in many datasets, which allowed an evaluation the effectiveness of our experiments in eliciting a response. Because non-responding datasets contribute variance to the correlation estimates, nuances in the response can be masked. Therefore, it may useful to perform a second analysis only on the datasets where there is an evident response. For example, when a second analysis was performed on datasets 1, 2, 5 and 6, the statistical significance of eigenvectors 1-4 increased and the statistical significance of subsequent eigenvectors decreased. Although this analysis did not result in a significant change in the spatial characteristics for these datasets, there may be cases where estimates could be improved with this approach.

Temporal correlations may be independent of the amplitude of the response. Therefore, the present invention can provide useful information even when response amplitudes vary from dataset to dataset as long as the temporal sequence of stimulation remains the same. In general, variance in response amplitude may come from intentional experimental design, such as dosage assays; thus, the present invention could be used to better estimate the minimum dosage of a drug at which a biological response is elicited. Variation in response may also occur as a result of uncontrollable experimental parameters such as inefficient or uneven cell loading or differential dye clearance.

The complete disclosure of the patents, patent documents, and publications cited in the Background, the Summary, the Detailed Description of Exemplary Embodiments, and elsewhere herein are incorporated by reference in their entirety as if each were individually incorporated. Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. Thus, the invention is limited only by the following claims and equivalents thereto.

What is claimed is:

1. A computer-implemented method for use in analysis of image data comprising:
   providing a ratiometric dataset representative of image data obtained over time for use in analysis of one or more objects of interest, wherein providing the ratiometric dataset comprises:
      providing a first wavelength dataset representative of a plurality of frames of image data taken over time at a first wavelength;
      providing a second wavelength dataset representative of a plurality of frames of image data taken over time at a second wavelength, wherein the image data for the second wavelength dataset is taken at the same time as the image data for the first wavelength dataset; and
      comparing the first wavelength dataset with the second wavelength dataset to provide the ratiometric dataset;
   generating a correlation matrix for the ratiometric dataset;
   generating a plurality of eigenvalues and a plurality of eigenvectors based on the correlation matrix;
   selecting a set of eigenvectors from the plurality of eigenvectors; and
   reconstructing a set of enhanced ratiometric images for use in analysis of the one or more objects of interest, wherein the set of enhanced ratiometric images is reconstructed using the set of eigenvectors, the first wavelength dataset, and the second wavelength dataset.

2. The method according to claim 1, wherein generating the correlation matrix for the ratiometric dataset comprises generating a temporal correlation matrix for the ratiometric dataset.

3. The method according to claim 1, wherein generating the correlation matrix for the ratiometric dataset comprises generating a spectral correlation matrix for the ratiometric dataset.

4. The method according to claim 3, wherein generating the spectral correlation matrix for the ratiometric dataset comprises:
   generating a spectral estimate dataset based on the ratiometric dataset; and
   generating the spectral correlation matrix based on the spectral estimate dataset.

5. The method according to claim 4, wherein generating the spectral correlation matrix based on the ratiometric dataset further comprises compressing the spectral estimate dataset using singular value decomposition.

6. The method according to claim 1, wherein providing the ratiometric dataset further comprises:
   standardizing the first wavelength dataset;
   standardizing the second wavelength dataset; and
   compressing the ratiometric dataset using singular value decomposition.

7. The method according to claim 1, wherein selecting the set of eigenvectors from the plurality of eigenvectors comprises comparing each of the eigenvalues of the plurality of eigenvalues to a threshold value.

8. The method according to claim 1, wherein reconstructing the set of enhanced ratiometric images comprises:
   generating a set of transformation vectors using the set of eigenvectors;
   generating a set of orthogonal basis transformation vectors based on the set of transformation vectors defining a subspace;
   projecting the first wavelength dataset and the second wavelength dataset onto the subspace defined by the set of orthogonal basis vectors resulting in projected image data; and
   using the projected image data to generate the set of enhanced ratiometric images.

9. The method according to claim 8, wherein the set of transformation vectors represents at least the spatial weights of pixels of the image data contributing to the correlation matrix.

10. The method according to claim 1, wherein the method further includes outputting one or more enhanced ratiometric images of the set of enhanced ratiometric images to at least one of a user, a display, and a file.

11. A computer-implemented method for use in analysis of image data comprising:
   providing two or more ratiometric datasets representative of image data obtained over time for use in analysis of one or more objects of interest, wherein providing each of the two or more ratiometric datasets comprises:
      providing a first wavelength dataset representative of image data taken over time at a first wavelength;
      providing a second wavelength dataset representative of image data taken over time at a second wavelength; and
      comparing the first wavelength dataset with the second wavelength dataset to provide each of the two or more ratiometric datasets;

generating a correlation matrix for each of the two or more ratiometric datasets;

generating a summed correlation matrix by summing the correlation matrices generated for each of the two or more ratiometric datasets;

generating a plurality of eigenvalues and a plurality of eigenvectors based on the summed correlation matrix;

selecting a set of eigenvectors from the plurality of eigenvectors; and reconstructing at least one set of enhanced ratiometric images for use in analysis of the one or more objects of interest, each set of enhanced ratiometric images corresponding to a ratiometric dataset of the two or more ratiometric datasets, wherein the at least one set of enhanced ratiometric images is reconstructed using the set of eigenvectors and the first and second wavelength dataset used to provide the corresponding ratiometric dataset.

12. The method according to claim 11, wherein generating the correlation matrix for each of the two or more ratiometric datasets comprises generating a temporal correlation matrix for each of the two or more ratiometric datasets.

13. The method according to claim 11, wherein generating the correlation matrix for each of the two or more ratiometric datasets comprises generating a spectral correlation matrix for each of the two or more ratiometric datasets.

14. The method according to claim 13, wherein generating the spectral correlation matrix for each of the two or more ratiometric datasets comprises:
    generating a spectral estimate dataset for each of the two or more ratiometric datasets; and
    generating the spectral correlation matrix based on the spectral dataset for each of the two or more ratiometric datasets.

15. The method according to claim 14, wherein generating the spectral correlation matrix for each of the two or more ratiometric datasets further comprises compressing the spectral estimate dataset for each of the two or more ratiometric datasets using singular value decomposition.

16. The method according to claim 11, wherein providing each of the two or more ratiometric datasets further comprises:
    standardizing the first wavelength dataset;
    standardizing the second wavelength dataset; and
    compressing each of the two or more ratiometric datasets using singular value decomposition.

17. The method according to claim 11, wherein selecting the set of eigenvectors from the plurality of eigenvectors comprises comparing each of the eigenvalues of the plurality of eigenvalues to a threshold value.

18. The method according to claim 11, wherein reconstructing at least one set of enhanced ratiometric images comprises:
    generating a set of transformation vectors for the corresponding ratiometric dataset using at least the set of eigenvectors;
    generating a set of orthogonal basis transformation vectors based on the set of transformation vectors for the corresponding ratiometric dataset defining a subspace;
    projecting the first and second wavelength dataset onto the subspace defined by the set of orthogonal basis vectors resulting in projected image data for each of the first and second wavelength datasets; and
    using the projected image data for each of the first and second wavelength datasets to generate the at least one set of enhanced ratiometric images.

19. The method according to claim 18, wherein the set of transformation vectors represents at least the spatial weights of pixels of the image data contributing to the correlation matrix for the corresponding ratiometric dataset.

20. The method according to claim 11, wherein each of the two or more ratiometric datasets comprises measurements to the same stimulus protocol.

21. The method according to claim 11, wherein the method further includes outputting one or more enhanced ratiometric images of the set of enhanced ratiometric images to at least one of a user, a display, and a file.

22. A computer-implemented method for use in analysis of measurement data comprising:
    providing one or more ratiometric datasets representative of measurement data obtained over time for use in analysis of one or more objects of interest, wherein providing each of the one or more the ratiometric datasets comprises:
        providing a first dataset representative of measurement data comprising a plurality of measurements taken at a plurality of different moments over time;
        providing a second dataset representative of measurement data comprising a plurality of measurements taken at a plurality of different moments over time, wherein the measurement data for the second dataset is taken at the same time as the measurement data for the first dataset; and
        comparing the first dataset with the second dataset to provide each of the one or more ratiometric datasets;
    generating a correlation matrix for the one or more ratiometric datasets;
    generating a plurality of eigenvalues and a plurality of eigenvectors based on the correlation matrix;
    selecting a set of eigenvectors from the plurality of eigenvectors; and
    reconstructing at least one set of enhanced ratiometric measurement data for use in analysis of the one or more objects of interest, each set of enhanced ratiometric measurement data corresponding to a ratiometric dataset of the one or more ratiometric datasets, wherein the at least one set of enhanced ratiometric measurement data is reconstructed using the set of eigenvectors and the first and second dataset used to provide the corresponding ratiometric dataset.

23. The method according to claim 22, wherein providing one or more ratiometric datasets comprises providing two or more ratiometric datasets, and wherein generating the correlation matrix for the one or more ratiometric datasets comprises:
    generating an individual correlation matrix for each of the two or more ratiometric datasets; and
    generating the correlation matrix by summing the individual correlation matrices generated for each of the two or more ratiometric datasets.

24. The method according to claim 22, wherein generating the correlation matrix for the one or more ratiometric datasets comprises generating a temporal correlation matrix for each of the one or more ratiometric datasets.

25. The method according to claim 22, wherein generating the correlation matrix for the one or more ratiometric datasets comprises generating a spectral correlation matrix for each of the one or more ratiometric datasets.

26. The method according to claim 25, wherein generating the spectral correlation matrix for each of the one or more ratiometric datasets comprises:
    generating a spectral estimate dataset for each of the one or more ratiometric datasets; and generating the spectral correlation matrix based on the spectral estimate dataset for each of the one or more ratiometric datasets.

27. The method according to claim 26, wherein generating the spectral correlation matrix for each of the one or more ratiometric datasets further comprises compressing the spectral estimate dataset for each of the one or more ratiometric datasets using singular value decomposition.

28. The method according to claim 22, wherein selecting the set of eigenvectors from the plurality of eigenvectors comprises comparing each of the eigenvalues of the plurality of eigenvalues to a threshold value.

29. The method according to claim 22, wherein reconstructing at least one set of enhanced ratiometric measurement data comprises:
generating a set of transformation vectors for the corresponding ratiometric dataset using at least the set of eigenvectors;
generating a set of orthogonal basis transformation vectors based on the set of transformation vectors for the corresponding ratiometric dataset defining a subspace;
projecting the first and second dataset onto the subspace defined by the set of orthogonal basis vectors resulting in projected measurement data for each of the first and second datasets; and
using the projected measurement data for each of the first and second datasets to generate the at least one set of enhanced ratiometric measurement data.

30. The method according to claim 22, wherein each of the one or more ratiometric sets comprises measurements to the same stimulus protocol.

31. The method according to claim 22, wherein the first dataset representative of the measurement data comprises a first wavelength dataset representative of a plurality of frames of image data taken over time at a first wavelength, and wherein the second dataset representative of the measurement data comprises a second wavelength dataset representative of a plurality of frames of image data taken over time at a second wavelength.

32. The method according to claim 22, wherein the method further includes outputting enhanced ratiometric measurement data of the at least one set of enhanced ratiometric data to at least one of a user, a display, and a file.

33. A computer program for use in conjunction with a processing apparatus to analyze ratiometric data, wherein the computer program is stored on a non-transitory computer readable storage medium and is operable when used with the processing apparatus to:
recognize one or more ratiometric datasets representative of measurement data obtained over time for use in analysis of one or more objects of interest, wherein each of the one or more ratiometric datasets comprises a first dataset representative of measurement data comprising a plurality of measurements taken at a plurality of different moments over time compared with a second dataset representative of measurement data comprising a plurality of measurements taken at a plurality of different moments over time, wherein the measurement data for the second dataset is taken at the same time as the measurement data for the first dataset;
generate a correlation matrix for the one or more ratiometric datasets;
generate a plurality of eigenvalues and a plurality of eigenvectors based on the correlation matrix;
select a set of eigenvectors from the plurality of eigenvectors; and
reconstruct at least one set of enhanced ratiometric measurement data for use in analysis of the one or more objects of interest, each set of enhanced ratiometric measurement data corresponding to a ratiometric dataset of the one or more ratiometric datasets, wherein the at least one set of enhanced ratiometric measurement data is reconstructed using the set of eigenvectors and the first and second dataset used to provide the corresponding ratiometric dataset.

34. The computer program according to claim 33, wherein the one or more ratiometric datasets comprises two or more ratiometric datasets, and wherein the computer program is further operable when used with the processing apparatus to:
generate an individual correlation matrix for each of the two or more ratiometric datasets; and
generate the correlation matrix by summing the individual correlation matrices generated for each of the two or more ratiometric datasets.

35. The computer program according to claim 33, wherein the correlation matrix for the one or more ratiometric datasets comprises a temporal correlation matrix for each of the one or more ratiometric datasets.

36. The computer program according to claim 33, wherein the correlation matrix for the one or more ratiometric datasets comprises a spectral correlation matrix for each of the one or more ratiometric datasets.

37. The computer program according to claim 36, wherein the computer program is further operable when used with the processing apparatus to:
generate a spectral estimate dataset for each of the one or more ratiometric datasets; and
generate the spectral correlation matrix based on the spectral estimate dataset for each of the one or more ratiometric datasets.

38. The computer program according to claim 37, wherein the computer program is further operable when used with the processing apparatus to compress the spectral estimate dataset for each of the one or more ratiometric datasets using singular value decomposition.

39. The computer program according to claim 33, wherein the computer program is further operable when used with the processing apparatus to compare each of the eigenvalues of the plurality of eigenvalues to a threshold value to select the set of eigenvectors from the plurality of eigenvectors.

40. The computer program according to claim 33, wherein the computer program is further operable when used with the processing apparatus to:
generate a set of transformation vectors for the corresponding ratiometric dataset using at least the set of eigenvectors;
generate a set of orthogonal basis transformation vectors based on the set of transformation vectors for the corresponding ratiometric dataset defining a subspace;
project the first and second dataset onto the subspace defined by the set of orthogonal basis vectors resulting in projected measurement data for each of the first and second datasets; and
use the projected measurement data for each of the first and second datasets to generate the at least one set of enhanced ratiometric measurement data.

41. The computer program according to claim 33, wherein each of the one or more ratiometric sets comprises measurements to the same stimulus protocol.

42. The computer program according to claim 33, wherein the first dataset representative of the measurement data comprises a first wavelength dataset representative of a plurality of frames of image data taken over time at a first wavelength, and wherein the second dataset representative of the measurement data comprises a second wavelength dataset representative of a plurality of frames of image data taken over time at a second wavelength.

43. The computer program according to claim 33, wherein the computer program is further operable when used with the processing apparatus to output enhanced ratiometric measurement data of the at least one set of enhanced ratiometric data using the processing apparatus to at least one of a user, a display, and a file.

* * * * *